(12) United States Patent
Berthelsen et al.

(10) Patent No.: US 7,259,244 B2
(45) Date of Patent: Aug. 21, 2007

(54) HUMAN HOMOLOGUE OF THE DBF4/ASK1 PROTEIN, NUCLEIC ACIDS, AND METHODS RELATED TO THE SAME

(75) Inventors: Jens Berthelsen, Milan (IT); Roberta Bosotti, Nerviano (IT); Antonella Isacchi, Milan (IT); Simon Plyte, Milan (IT)

(73) Assignee: Nerviano Medical Sciences S.R.L., Nerviano, Milan (IT)

( * ) Notice: Subject to any disclaimer, the term of this patent is extended or adjusted under 35 U.S.C. 154(b) by 316 days.

(21) Appl. No.: 10/311,401

(22) PCT Filed: Jun. 15, 2001

(86) PCT No.: PCT/EP01/06880

§ 371 (c)(1),
(2), (4) Date: Jun. 27, 2003

(87) PCT Pub. No.: WO01/96557

PCT Pub. Date: Dec. 20, 2001

(65) Prior Publication Data

US 2004/0102611 A1 May 27, 2004

Related U.S. Application Data

(63) Continuation-in-part of application No. 09/595,683, filed on Jun. 16, 2000, now abandoned.

(51) Int. Cl.
*A61K 38/16* (2006.01)
*C07K 1/00* (2006.01)
*C07K 16/00* (2006.01)
*C07H 21/04* (2006.01)

(52) U.S. Cl. .................. 530/358; 350/388.23; 536/23.5
(58) Field of Classification Search ................ 530/350, 530/358, 388.23; 536/23.5
See application file for complete search history.

(56) References Cited

U.S. PATENT DOCUMENTS

| 4,399,216 A | 8/1983 | Axel et al. |
| 4,518,584 A | 5/1985 | Mark et al. |
| 4,683,195 A | 7/1987 | Mullis et al. |
| 4,683,202 A | 7/1987 | Mullis |
| 4,737,462 A | 4/1988 | Mark et al. |
| 4,879,236 A | 11/1989 | Smith et al. |

FOREIGN PATENT DOCUMENTS

| EP | 0 367 566 | 5/1990 |
| WO | WO91/18982 | 12/1991 |

OTHER PUBLICATIONS

Montagnoli C. et al. Drf1, a novel regulatory subunit for human Cdc7 kinase, EMBO J. 2002, 21, 3171-3181.*

Altschul, et al., "Gapped BLAST and PSI-BLAST: a new generation of protein database search programs," Nuc. Acids Res. (1997) 25(17):3389-3402.
Altschul, et al., "Basic Local Alignment Search Tool," J. Mol. Biol. (1990) 215:403-410.
Birren, et al., EMBL Accession No. AC005810, Jun. 29, 1998.
Anderson, "Human Gene Therapy," Science (1992) 256:808-813.
NCI-CGAP, EMBL Accession No. AA622743, Oct. 16, 1997.
Bauer, et al., "A genetic enrichment for mutations constructed by oligodeoxynucleotide-directed mutagenesis," Gene (1985) 37:73-81.
Benoist, et al., "In vivo sequence requirements of the SV40 eary promoter region," Nature (1981) 290:304-310.
Dias Neto, et al., EMBL Accession No. AW886993, May 25, 2000.
Bowie, et al., "Deciphering the Message in Protein Sequences: Tolerance to Amino Acid Substitutions," Science (1990) 247:1306-1310.
Breeden, et al., "Regulation of the Yeast HO Gene," Cold Spring Harbor Symp. Quant. Biol. (1985) 50:643-650.
Cosman, et al., "Cloning, sequence and expression of human interleukin-2 receptor," Nature (1984) 312-768-771.
Ausubel, F.M., et al., in Short protocols in molecular biology, John Wiley and Sons, NY, 1999.
Eisenthal, R., et al., in Enzyme Assays: A Practical Approach, Oxford University Press, 1992.
Harlow, E., et al., in ANTIBODIES: A Laboratory Manual, Cold Spring Harbor Laboratory, Cold Spring Harbor, NY, 1988.
Hendrix, R.W., (ed.) Lambda II, Cold Spring Harbor Press, Cold Spring Harbor, NY, 1980.
Hershey, A.D., (ed.), The Bacteriophage Lambda, Cold Spring Harbor Press, Cold Spring Harbor, NY, 1973.
O'Reilly, et al., (eds.), in Baculovirus Expression Vectors: A Laboratory Manual, W.H. Freeeman & Co., NY, 1992.
Osol, A., (ed.), in Remington's Pharmaceutical Sciences, 16th edition, 1980.
Kruse, et al., (eds.) in Tissue Culture, Academic Press, 1973.
Current Protocols in Molecular Biology, (1999) John Wiley and Sons (pub.).
Abelson, et al. (eds.) Methods in Enzymology (1997) Academic Press.

(Continued)

*Primary Examiner*—Rebecca E. Prouty
*Assistant Examiner*—Malgorzata Walicka
(74) *Attorney, Agent, or Firm*—Scully, Scott, Murphy & Presser, P.C

(57) ABSTRACT

The present invention provides a human polypeptide homolog of DBF4/ASK1 (for "Activator of S phase kinase") and polynucleotides which identify and encode DRF1 (for "DBF4 Related Factor 1"). In addition, the invention provides expression vectors, host cells and methods for its production. The invention also provides methods for the identification of DRF1 or DRF1-containing complex agonists/antagonists, useful for the treatment of human diseases and conditions.

5 Claims, 8 Drawing Sheets

OTHER PUBLICATIONS

Berger, et al, "Guide to Molecular Cloning Techniques," Methods in Enzymol. 152, Academic Press, Inc.

Hunter, et al., eds., Methods in Enzmol. (1991) Academc Press.

Pagano, M. (ed.) "Cell Cycle: Materials and Methods," 1995 Springer-Verlag.

Sambrook, et al., "Molecular Cloning: A Laboratory Manual," 2nd Ed., Cold Spring Harbor Press, 1989.

Smith, et al., "Genetic Engineering: Principles and Methods," Plenum 1991.

Stiites, et al., (eds.), Basic and Clinical Immunology (4th ed.) Lange Medical Publications.

Lei, A.M., "Mcm2 is a target of regulation by Cdc7-Dbf4 during the initiation of DNA synthesis," Genes Dev. (1997) 11:3365-3374.

Masai, H., et al., "hsk1+, a Schizosaccharomyces pombe gene related to *Saccharomyces cervisiae* CDC7, is required for chromosomal replication," EMBO J. (1995) 14(13):3094-3104.

Newton, C.S., "Putting it all together:building a prereplicative complex," Cell (1997) 91:717-720.

Sato, N., et al., "Human and Xenopus cDNAs encoding budding yeast Cdc7-related kinases: in vitro phosphorylation of MCM subunits by a putative human homologue of Cdc7," EMBO J. (1997) 16(14):4340-4351.

Smith, T.F., et al., "Comparison of biosequences," Adv. Appl. Math. (1981) 2:482-489.

Stillman, B., "Cell cycle control of DNA replication," Science (1996) 274:1659-1664.

Bousset, K., et al., "The Cdc7 protein kinase is required for origin firing during S phase," Genes Dev. (1998) 12:480-490, 1072.

Burge, et al., "Prediction of complete gene structures in human genomic DNA," J. Mol. Biol. (1997) 268:78-94.

Diffley, J.F.X., et al., "Two steps in the assembly of complexes at yeast replication origins in vivo," Cell (1994) 78:303-316.

Donaldson, A.D., "Cdc7 is required throughout the yeast S phase to activate replication origins," Genes Dev. (1998) 12:491-501.

Dowell, S.J., et al., "Interaction of Dbf4, Cdc7 protein kinase regulatory subunit, with yeast replication origins in vivo," Science (1994) 265:1243-1246.

Hardy, C.F.J., et al., "mcm5/cdc46-bob-1 bypasses the requirement for the S phase activator Cdc7p," Proc.Natl. Acad. Sci. (1997) 94:3151-3155.

Hess, G.F., "A human homolog of the yeast CDC7 gene is overexpressed in some tumors and transformed cell lines," Gene (1998) 211:133-140.

Jiang, W., et al., "Identification and characterization of a human protein kinase related to budding yeast Cdc7p," Paroc. Natl. Acad. Sci. USA (1997) 94:14320-14325.

Jiang, et al., "Mammalian Cdc7-Dbf4 protein kinase complex is essential for initiation of DNA replication," EMBO J. (1999) 18:5703-5713.

Kim, J.M., et al., "Growth regulation of the expression of mouse cDNA and gene encoding a serine/threonine kinase related to *Saccharomyces cervisiae* CDC7essential for G1/S transition," J. Biol. Chem. (1998) 273(36):233248-23257.

Kumagai, H., et al., "A novel growth and cell cycle-regualted protein, ASK, activates human Cdc7-related kinase and is essential for G1/S transition in mammalian cells," Mol. Cell. Biol. (1999) 19(7):5083-5095.

Cosman, et al., "High Level stable Expression of Human Interleukin-2 Receptors in Mouse Cells Generates Only Low Affinity Interleukin-2 Binding Sites," Mol. Immunol. (1986) 23(9):935-941.

Craik, "Use of Oligonucleotides for Site-Specific Mutagenesis," BioTechniques (1985) Jan./Feb. 12-19.

Fields, et al., "A novel genetic system defect protein-protein interactions," Nature (1989) 340:245-246.

Henikoff, et al., Amino acid substitution matrices from protein blocks, Proc. Natl. Acad. Sci, USA (1992) 89:10915-10919.

Huse, et al., "Generation of a Large Combinatorial Library of the Immunoglobulin Repetoire in Phage Lambda," *Science* (1989) 246:1275-1281.

Karlin, et al., "Applications and statistics for multiple high-scoring segments in molecular sequences," Proc. Natl. Acad. Sci. USA (1993) 90:5873-5877.

Lin, et al., "The Oxazolidinone Eperezolid Binds to the 50s Ribosomal Subunit and Competes with Binding of Chloramphenicol and Lincomycin," Antimicrob. Agents Chemother. (1997) 41(10):2127-2131.

Luckow, et al., "Trends in the Development of Baculovirus Expression Vectors," Bio/Technology (1988) 6:47-55.

Okayama, et al., "A cDNA Cloning Vector That Permits Expression of cDNA Inserts in Mammalian Cells," Mol. Cell Biol. (1983) 3(2)280-289.

Summers, et al., "A Manual of Methods for Baculovirus Vectors and Insect Cell Culture Procedures," Texas Argic. Exptal. Station Bull. No. 1555 (1987) 1-56.

Walder, et al., "Oligodeoxynucleotide-directed mutagenesis using the yeast transformation system," Gene (1986) 42:133-139.

\* cited by examiner

SEQUENCE LISTING

<160> NUMBER OF SEQ ID NOS: 13

<210> SEQ ID NO 1
<211> LENGTH: 3003
<212> TYPE: DNA
<213> ORGANISM: Homo sapiens

<400> SEQUENCE: 1
aaaacgccaa gagattgatg ctgtagctgc cctgagataa ccaggactgt ggaatcggga     60
agagctcatg gagctcgcga atgtaatacg gaggcctctg aggaaggagt acggaggccg    120

-continued

| | |
|---|---|
| agaaggagcc ggcatttgat gagcgaaccg ggaaagggag acgattgcct cgagctggag | 180 |
| agttccatgg ctgagagtag gctccgggcc ccggacctag gagtttccag gtgtctagga | 240 |
| aaatgccaga agaactcacc aggtgccagg aagcatccct tttccggaaa gtccttttac | 300 |
| ttggatctgc ctgctggcaa gaatctccag tttttgacgg gggccattca gcaactgggt | 360 |
| ggggtaattg agggttttct gagcaaagaa gtaagttaca tcgtgtccag ccgcagagaa | 420 |
| gtaaaggcag agagcagtgg gaaaagccat agaggctgcc ctagccctag ccccagtgag | 480 |
| gtcagagtgg aaacatcggc catggttgat ccaaaaggca gccacccag gccttcacgg | 540 |
| aaacccgttg actcggtgcc tctaagcaga gggaaggagc tgctgcagaa ggctatcaga | 600 |
| aaccagggga gcatcagtgg aggaggcagt gggggcagca gcagcctcct gaccaatgcc | 660 |
| cgctcttggg gagtgaggat tctgcacgtg atgaaatga tgatgcacgt gcaacagctg | 720 |
| tctcttgcgt ctttatgtgt gaaaaaacaa cagccaaaga agccagaggg aacatgtcca | 780 |
| gcagcagagt caagaacacg gaaagtggcc agactgaagg ccccgttcct caaaatcgaa | 840 |
| gatgaaagca ggaagtttcg tcctttccat catcagttta aatcctttcc tgaaatttct | 900 |
| tttcttggac ccaaagatgc aagtcccttt gaggccccga cgaccctggg cagcatgcac | 960 |
| cataccagag aatccaagga tggagagcca agcccacgat cagctgccca ccatgccc | 1020 |
| aggaggaaga aaggctactg cgagtgctgt caggaggcct tcgaggagct ccatgtgcat | 1080 |
| cttcagagtg cccagcaccg gagctttgcc ctggaagccc atctatatgc agaagtggac | 1140 |
| aggatcattg ctcagctcag ccacagcttt gcagacatcc cttccaggc tggcctcccc | 1200 |
| aggtggtcag gttccccagc ttctgattgt gaccctctct gtcctgagac tctgcacccc | 1260 |
| catcagccct cccatcccag ggcagcatct cccaggataa ggaaagaaga cagctgccag | 1320 |
| gcatcagtga cccaaggcag ggctgcgggc cagcagcgat ggacagaatc actagatggt | 1380 |
| gtgatgggac ctcctgcaag tcacacatgt gtgagtgcca caaccctcct gccggccttg | 1440 |
| cccaagggct ccagggagca gggctgcctc tgtccctgcc cagcctcctt tacccagtct | 1500 |
| catctggtca cttccttggc tctgctgcct ggggagtggt cgcctgcaga ggacatgccc | 1560 |
| ctccatccct cccaagaaaa ctcctttgcc ccggcggaca ttcctgttaa gggcccactc | 1620 |
| ctcttccctg aagccagacc gtggcttatg tctgcacgct gctgggttcg tccctttcct | 1680 |
| tttgtgacat ggggttgcct cattccccat gacaccaccc ctctgcatga ggaagtttcc | 1740 |
| ccttgcccct gtctcagact tggataccct tacctgctgc tcacacaaag cctgtggtgc | 1800 |
| cgggttcggg tgccctcatt gtcaactgca ggacccattc cccgaacctc acatccgtgt | 1860 |
| acccttgcct tcccctccta tctcaatgat catgaccttg gacatctctg ccaggccaaa | 1920 |
| ccccaaggct ggaacactcc tcagccattt ctccattgcg gcttcctggc tgtagactca | 1980 |
| ggttagaggt gaacccagaa cacctgagac ttgacccagg atggatgggt gctgcttgat | 2040 |
| gtgaatgagg tcccgcagtg gctccttggc gtgagcactc tcagactcc tttccactcc | 2100 |
| agccccttt ccacatcgca ccagatgact tttacccaga cccagtgggc attgccttat | 2160 |
| cttgcagtca gtccctttc aacatgttgc cgtttctttc tgaagaggtg tcctccctcc | 2220 |
| acaagtcaca ctgtctgtcc ctggccctcc agcccacctc gccaaccact cttgttggtt | 2280 |
| tccttctcag acttgccacc tttccctct gcccaaaat gccatgctcc tctcctggaa | 2340 |
| aacacttgag ttgattcagt aaatcgactt caaatacttg aaggctccca ccttctgttc | 2400 |
| tctggctcct tcctgcggtc tatacctacc gcctcctctt cacctcctc ccttccacac | 2460 |
| ttccttcctg ggtagctctg cctgaagcat tccactaaga tcatctattc caaggtcatg | 2520 |

```
gacaggctac tggtgaccaa agttggttcc ttttctcctt tctttcctcc ttgaagcctg    2580
gctcccttgg tcgcagcagc ccctcagtgg cctggttctc ctgtcccct gcccttcctc    2640 accattgccc attccctcgt tcgttcattc agcacaggcc ttgccgtctg ccctgagtca    2700
gctccgagac acctgaagag ccctccagcc ctaactactt tactcagact aggtccccag    2760
gcctttgttc ttgcctcttc tcgctgagcc tttcacttct cggcagatgt gaccgattgg    2820
tagctccacc ccaactccct tctgctgggt ggaatgcagg agctagctgc ctccaactca    2880
ctgtgacctc agaaaaatgc ctttattact cgggcctcag tttcctcgtc tttaagtaag    2940
gggcttggat gagatgattt caggacccctt tccaataata aaatactgtg actgccaaaa    3000
aaa                                                                  3003

<210> SEQ ID NO 2
<211> LENGTH: 1845
<212> TYPE: DNA
<213> ORGANISM: Homo sapiens

<400> SEQUENCE: 2
atgagcgaac cgggaaaggg agacgattgc ctcgagctgg agagttccat ggctgagagt      60
aggctccggg ccccggacct aggagttttcc aggtgtctag aaaatgccaa gaagaactca    120
ccaggtgcca ggaagcatcc cttttccgga aagtcctttt acttggatct gcctgctggc    180
aagaatctcc agttttttgac gggggccatt cagcaactgg gtggggtaat tgagggtttt    240
ctgagcaaag aagtaagtta catcgtgtcc agccgcagag aagtaaaggc agagagcagt    300
gggaaaagcc atagaggctg ccctagccct agccccagtg aggtcagagt ggaaacatcg    360
gccatggttg atccaaaagg cagccacccc aggccttcac ggaaacccgt tgactcggtg    420
cctctaagca gagggaagga gctgctgcag aaggctatca gaaaccaggg gagcatcagt    480
ggaggaggca gtgggggcag cagcagcctc ctgaccaatg cccgctcttg gggagtgagg    540
attctgcacg tggatgaaat gatgatgcac gtgcaacagc tgtctcttgc gtctttatgt    600
gtgaaaaaac aacagccaaa gaagccgagg ggaacatgtc cagcagcaga gtcaagaaca    660
cggaaagtgg ccagactgaa ggccccgttc ctcaaaatcg aagatgaaag caggaagttt    720 cgtccttttcc atcatcagtt taaatccttt cctgaaattt cttttcttgg acccaaagat    780
gcaagtccct ttgaggcccc gacgaccctg gcagcatgc accataccag agaatccaag    840
gatggagagc caagcccacg atcagctgcc cacaccatgc caggaggaa gaaaggctac    900 tgcgagtgct gtcaggaggc cttcgaggag ctccatgtgc atcttcagag tgcccagcac    960
cggagctttg ccctggaagc ccatctatat gcagaagtgg acaggatcat tgctcagctc    1020
agccacagct ttgcagacat cccttttccag gctggcctcc ccaggtggtc aggttcccca    1080
gcttctgatt gtgaccctct ctgtcctgag actctgcacc ccatcagcc ctcccatccc    1140 agggcagcat ctcccaggat aaggaaagaa gacagctgcc aggcatcagt gacccaaggc    1200
agggctgcgg gccagcagcg atggacagaa tcactagatg gtgtgatggg acctcctgca    1260
agtcacacat gtgtgagtgc cacaaccctc ctgccggcct tgcccaaggg ctccagggag    1320
cagggctgcc tctgtccctg cccagcctcc tttacccagt ctcatctggt cacttccttg    1380
gctctgctgc ctggggagtg gtcgcctgca gaggacatgc ccctccatcc ctcccaagaa    1440
aactcctttg ccccggcgga cattcctgtt aagggcccac tcctcttccc tgaagccaga    1500
ccgtggctta tgtctgcacg ctgctggggtt cgtcccttttc cttttgtgac atggggttgc    1560
```

-continued

```
ctcattcccc atgacaccac ccctctgcat gaggaagttt cccccttgccc ctgtctcaga      1620 cttggatacc tttacctgct gctcacacaa agcctgtggt gccgggttcg ggtgccctca      1680
ttgtcaactg caggacccat tccccgaacc tcacatccgt gtaccccttgc cttcccctcc    1740 tatctcaatg atcatgacct tggacatctc tgccaggcca aaccccaagg ctggaacact     1800
cctcagccat ttctccattg cggcttcctg gctgtagact caggt                     1845
```

<210> SEQ ID NO 3
<211> LENGTH: 615
<212> TYPE: PRT
<213> ORGANISM: Homo sapiens

<400> SEQUENCE: 3

```
Met Ser Glu Pro Gly Lys Gly Asp Asp Cys Leu Glu Leu Glu Ser Ser
  1               5                  10                  15

Met Ala Glu Ser Arg Leu Arg Ala Pro Asp Leu Gly Val Ser Arg Cys
             20                  25                  30

Leu Gly Lys Cys Gln Lys Asn Ser Pro Gly Ala Arg Lys His Pro Phe
         35                  40                  45

Ser Gly Lys Ser Phe Tyr Leu Asp Leu Pro Ala Gly Lys Asn Leu Gln
     50                  55                  60

Phe Leu Thr Gly Ala Ile Gln Gln Leu Gly Gly Val Ile Glu Gly Phe
 65                  70                  75                  80

Leu Ser Lys Glu Val Ser Tyr Ile Val Ser Arg Arg Glu Val Lys
                 85                  90                  95

Ala Glu Ser Ser Gly Lys Ser His Arg Gly Cys Pro Ser Pro Ser Pro
            100                 105                 110

Ser Glu Val Arg Val Glu Thr Ser Ala Met Val Asp Pro Lys Gly Ser
        115                 120                 125

His Pro Arg Pro Ser Arg Lys Pro Val Asp Ser Val Pro Leu Ser Arg
    130                 135                 140

Gly Lys Glu Leu Leu Gln Lys Ala Ile Arg Asn Gln Gly Ser Ile Ser
145                 150                 155                 160

Gly Gly Gly Ser Gly Gly Ser Ser Ser Leu Leu Thr Asn Ala Arg Ser
                165                 170                 175

Trp Gly Val Arg Ile Leu His Val Asp Glu Met Met Met His Val Gln
            180                 185                 190

Gln Leu Ser Leu Ala Ser Leu Cys Val Lys Lys Gln Pro Lys Lys
        195                 200                 205

Pro Glu Gly Thr Cys Pro Ala Ala Glu Ser Arg Thr Arg Lys Val Ala
    210                 215                 220

Arg Leu Lys Ala Pro Phe Leu Lys Ile Glu Asp Glu Ser Arg Lys Phe
225                 230                 235                 240

Arg Pro Phe His His Gln Phe Lys Ser Phe Pro Glu Ile Ser Phe Leu
                245                 250                 255

Gly Pro Lys Asp Ala Ser Pro Phe Glu Ala Pro Thr Thr Leu Gly Ser
            260                 265                 270

Met His His Thr Arg Glu Ser Lys Asp Gly Glu Pro Ser Pro Arg Ser
        275                 280                 285

Ala Ala His Thr Met Pro Arg Arg Lys Lys Gly Tyr Cys Glu Cys Cys
    290                 295                 300

Gln Glu Ala Phe Glu Glu Leu His Val His Leu Gln Ser Ala Gln His
305                 310                 315                 320

Arg Ser Phe Ala Leu Glu Ala His Leu Tyr Ala Glu Val Asp Arg Ile
```

-continued

```
                            325                 330                 335
            Ile Ala Gln Leu Ser His Ser Phe Ala Asp Ile Pro Phe Gln Ala Gly
                            340                 345                 350

Leu Pro Arg Trp Ser Gly Ser Pro Ala Ser Asp Cys Asp Pro Leu Cys
                            355                 360                 365

Pro Glu Thr Leu His Pro His Gln Pro Ser His Pro Arg Ala Ala Ser
                            370                 375                 380

Pro Arg Ile Arg Lys Glu Asp Ser Cys Gln Ala Ser Val Thr Gln Gly
            385                 390                 395                 400

Arg Ala Ala Gly Gln Gln Arg Trp Thr Glu Ser Leu Asp Gly Val Met
                            405                 410                 415

Gly Pro Pro Ala Ser His Thr Cys Val Ser Ala Thr Thr Leu Leu Pro
                            420                 425                 430

Ala Leu Pro Lys Gly Ser Arg Glu Gln Gly Cys Leu Cys Pro Cys Pro
                            435                 440                 445

Ala Ser Phe Thr Gln Ser His Leu Val Thr Ser Leu Ala Leu Leu Pro
                            450                 455                 460

Gly Glu Trp Ser Pro Ala Glu Asp Met Pro Leu His Pro Ser Gln Glu
            465                 470                 475                 480

Asn Ser Phe Ala Pro Ala Asp Ile Pro Val Lys Gly Pro Leu Leu Phe
                            485                 490                 495

Pro Glu Ala Arg Pro Trp Leu Met Ser Ala Arg Cys Trp Val Arg Pro
                            500                 505                 510

Phe Pro Phe Val Thr Trp Gly Cys Leu Ile Pro His Asp Thr Thr Pro
                            515                 520                 525

Leu His Glu Glu Val Ser Pro Cys Pro Cys Leu Arg Leu Gly Tyr Leu
                            530                 535                 540

Tyr Leu Leu Leu Thr Gln Ser Leu Trp Cys Arg Val Arg Val Pro Ser
            545                 550                 555                 560

Leu Ser Thr Ala Gly Pro Ile Pro Arg Thr Ser His Pro Cys Thr Leu
                            565                 570                 575

Ala Phe Pro Ser Tyr Leu Asn Asp His Asp Leu Gly His Leu Cys Gln
                            580                 585                 590

Ala Lys Pro Gln Gly Trp Asn Thr Pro Gln Pro Phe Leu His Cys Gly
                            595                 600                 605

Phe Leu Ala Val Asp Ser Gly
            610                 615

<210> SEQ ID NO 4
<211> LENGTH: 2854
<212> TYPE: DNA
<213> ORGANISM: Homo sapiens

<400> SEQUENCE: 4
gggagacgat tgcctcgagc tggagagttc catggctgag agtaggctcc gggccccgga      60
cctaggagtt ccaggtgtc taggaaaatg ccagaagaac tcaccaggtg ccaggaagca     120 tccctttttcc ggaaagtcct tttacttgga tctgcctgct ggcaagaatc tccagttttt    180
gacgggggcc attcagcaac tgggtggggt aattgagggt tttctgagca aagaagtaag    240
ttacatcgtg tccagccgca gagaagtaaa ggcagagagc agtgggaaaa gccatagagg    300
ctgccctagc cctagcccca gtgaggtcag agtgaaaaca tcggccatgg ttgatccaaa    360
aggcagccac cccaggcctt cacgaaaacc cgttgactcg gtgcctctaa gcagagggaa    420
ggagctgctg cagaaggcta tcagaaacca ggggagcatc agtggaggag gcagtggggg    480
```

-continued

```
cagcagcagc ctcctgacca atgcccgctc ttggggagtg aggattctgc acgtggatga    540
aatgatgatg cacgtgcaac agctgtctct tgcgtcttta tgtgtgaaaa acaacagcc     600 aaagaagcca gagggaacat gtccagcagc agagtcaaga acacggaaag tggccagact    660
gaaggccccg ttcctcaaaa tcgaagatga agcaggaag tttcgtcctt ccatcatca      720 gtttaaatcc tttcctgaaa tttcttttct tggacccaaa gatgcaagtc cctttgaggc    780
cccgacgacc ctgggcagca tgcaccatac agagaatcc aaggatggag agccaagccc     840
acgatcagct gccccacacca tgcccaggag gaagaaaggc tactgcgagt gctgtcagga   900
ggccttcgag gagctccatg tgcatcttca gagtgcccag caccggagct tgccctgga    960 agcccatcta tatgcagaag tggacaggat cattgctcag ctcagccaca gctttgcaga   1020 catcccttt caggctggcc tccccaggtg gtcaggttcc ccagcttctg attgtgaccc     1080
tctctgtcct gagactctgc accccatca gccctccat cccagggcag catctcccag     1140
gataaggaaa gaagacagct gccaggcatc agtgacccaa ggcagggctg cgggccagca   1200
gcgatggaca gaatcactag atggtgtgat gggacctcct gcaagtcaca catgtgtgag   1260
tgccacaacc ctcctgccgg ccttgcccaa gggctccagg gagcagggct gcctctgtcc    1320
ctgcccagcc tccttaccc agtctcatct ggtcacttcc ttggctctgc tgcctgggga    1380
gtggtcgcct gcagaggaca tgcccctcca tccctcccaa gaaaactcct ttgccccggc    1440
ggacattcct gttaagggcc cactcctctt ccctgaagcc agaccgtggc ttatgtctgc    1500
acgctgctgg gttcgtccct ttccttttgt gacatggggt tgcctcattc cccatgacac    1560 caccccctctg catgaggaag tttccccttg ccctgtctc agacttggat acctttacct   1620
gctgctcaca caaagcctgt ggtgccgggt tcgggtgccc tcattgtcaa ctgcaggacc    1680
cattccccga acctcacatc cgtgtaccct tgccttcccc tcctatctca atgatcatga   1740
ccttggacat ctctgccagg ccaaacccca aggctggaac actcctcagc catttctcca   1800
ttgcggcttc ctggctgtag actcaggtta gaggtgaacc cagaacacct gagacttgac    1860
ccaggatgga tgggtgctgc ttgatgtgaa tgaggtcccg cagtggctcc ttggcgtgag    1920
cactgctcag actcctttcc actccagccc cctttccaca tcgcaccaga tgactttac    1980 ccagacccag tggcattgc cttatcttgc agtcagtccc ttttcaacat gttgccgttt    2040 cttttctgaag aggtgtcctc cctccacaag tcacactgtc tgtccctggc cctccagccc   2100
acctcgccaa ccactcttgt tggtttcctt ctcagacttg ccaccttcc cctctgcccc    2160 aaaatgccat gctcctctcc tggaaaacac ttgagttgat tcagtaaatc gacttcaaat    2220
acttgaaggc tccaccttc tgttctctgg ctccttcctg cggtctatac ctaccgcctc    2280
ctcttcacct ccttcccttc cacacttcct tcctgggtag ctctgcctga agcattccac    2340
taagatcatc tattccaagg tcatggacag gctactggtg accaaagttg gttccttttc   2400
tcctttcttt cctccttgaa gcctggctcc cttggtcgca gcagcccctc agtggcctgg    2460
ttctcctgtc cccctgccct tcctcaccat tgcccattcc ctcgttcgtt cattcagcac    2520
aggccttgcc gtctgccctg agtcagctcc gagacacctg aagagccctc cagccctaac    2580
tactttactc agactaggtc cccaggcctt tgttcttgcc tcttctcgct gagccttca    2640 cttctcggca gatgtgaccg attggtagct ccaccccaac tcccttctgc tgggtggaat   2700
gcaggagcta gctgcctcca actcactgtg acctcagaaa aatgccttta ttactcgggc   2760 ctcagttttcc tcgtctttaa gtaagggct tggatgagat gatttcagga ccctttccaa   2820
```

-continued

| taataaaata ctgtgactgc caaaaaaaaa aaaa | 2854 |

<210> SEQ ID NO 5
<211> LENGTH: 3002
<212> TYPE: DNA
<213> ORGANISM: Homo sapiens

<400> SEQUENCE: 5

| ggctcgaggc cggcaggaaa tttaaactga agccgcggcc gaaaacgcca agagattgat | 60 |
| gctgtagctg ccctgagata accaggactg tggaatcggg aagagctcat ggagctcgcg | 120 |
| aatgtaatac ggaggcctct gaggaaggag tacggaggcc gagaaggagc cggcatttga | 180 |
| tgagcgaacc gggaaaggga gacgattgcc tcgagctgga gagttccatg gctgagagta | 240 |
| ggctccgggc cccggaccta ggagtttcca ggtgtctagg aaaatgccag aagaactcac | 300 |
| caggtgccag gaagcatccc ttttccggaa agtcctttta cttggatctg cctgctggca | 360 |
| agaatctcca gttttttgacg ggggccattc agcaactggg tggggtaggt aattgagggt | 420 |
| tttctgagca aagaagtaag ttacatcgtg tccagccgca gagaagtaaa ggcagagagc | 480 |
| agtgggaaaa gccatagagg ctgccctagc cctagcccca gtgaggtcag agtggaaaca | 540 |
| tcggccatgg ttgatccaaa aggcagccac cccaggcctt cacggaaacc cgttgactcg | 600 |
| gtgcctctaa gcagagggaa ggagctgctg cagaaggcta tcagaaacca gaatgatga | 660 |
| tgcacgtgca acagctgtct cttgcgtctt tatgtgtgaa aaaacaacag ccaaagaagc | 720 |
| cagagggaac atgtccagca gcagagtcaa gaacacggaa agtggccaga ctgaaggccc | 780 |
| cgttcctcaa aatcgaagat gaaagcagat gcaagtccct ttgaggcccc gacgaccctg | 840 |
| ggcagcatgc accataccag agaatccaag gatggagagc caagcccacg atcagctgcc | 900 |
| cacaccatgc ccaggaggaa gaaaggctac tgcgagtgct gtcaggaggc cttcgaggag | 960 |
| ctccatgtgc atcttcagag tgcccagcac cggagctttg ccctggaagc ccatctatat | 1020 |
| gcagaagtgg acaggatcat tgctcagctc agccacagct ttgcagacat cccttttccag | 1080 |
| gctggcctcc ccaggtggtc aggttcccca gcttctgatt gtgaccctct ctgtcctgag | 1140 |
| actctgcacc cccatcagcc ctcccatccc agggcagcat ctcccaggat aaggaaagaa | 1200 |
| gacagctgcc aggcatcagt gacccaaggc agggctgcgg gccagcagcg atggacagaa | 1260 |
| tcactagatg gtgtgatggg acctcctgca agtcacacat gtgtgagtgc acaacccctc | 1320 |
| ctgccggcct tgcccaaggg ctccaggag cagggctgcc tctgtccctg cccagcctcc | 1380 |
| tttacccagt ctcatctggt cacttccttg gctctgctgc ctggggagtg gtcgcctgca | 1440 |
| gaggacatgc ccctccatcc ctcccaagaa aactcctttg ccccggcgga cattcctgtt | 1500 |
| aagggcccac tcctcttccc tgaagccaga ccgtggctta tgtctgcacg ctgctgggtt | 1560 |
| cgtcccttttc cttttgtgac atggggttgc ctcattcccc atgacaccac ccctctgcat | 1620 |
| gaggaagttt ccccttgccc ctgtctcaga cttggatacc tttacctgct gctcacacaa | 1680 |
| agcctgtggt gccgggttcg ggtgccctca ttgtcaactg caggacccat tccccgaacc | 1740 |
| tcacatccgt gtaccttgc cttccctcc tatctcaatg atcatgacct ggacatctc | 1800 |
| tgccaggcca aaccccaagg ctggaacact cctcagccat ttctccattg cggcttcctg | 1860 |
| gctgtagact caggttagag gtgaacccag aacacctgag acttgaccca ggatggatgg | 1920 |
| gtgctgcttg atgtgaatga ggtcccgcag tggctccttg gcgtgagcac tgctcagact | 1980 |
| cctttccact ccagcccct ttccacatcg caccagatga cttttaccca gacccagtgg | 2040 |
| gcattgcctt atcttgcagt cagtcccttt tcaacatgtt gccgtttctt tctgaagagg | 2100 |

```
tgtcctccct ccacaagtca cactgtctgt ccctggccct ccagcccacc tcgccaacca    2160
ctcttgttgg tttccttctc agacttgcca cctttcccct ctgccccaaa atgccatgct    2220
cctctcctgg aaaacacttg agttgattca gtaaatcgac ttcaaatact tgaaggctcc    2280
caccttctgt tctctggctc cttcctgcgg tctataccta ccgcctcctc ttcacctcct    2340
tcccttccac acttccttcc tgggtagctc tgcctgaagc attccactaa gatcatctat    2400
tccaaggtca tggacaggct actggtgacc aaagttggtt cctttctcc tttctttcct     2460 ccttgaagcc tggctccctt ggtcgcagca gcccctcagt ggcctggttc tcctgtcccc    2520
ctgcccttcc tcaccattgc ccattccctc gttcgttcat tcagcacagg ccttgccgtc    2580
tgccctgagt cagctccgag acacctgaag agccctccag ccctaactac tttactcaga    2640
ctaggtcccc aggcctttgt tcttgcctct tctcgctgag cctttcactt ctcggcagat    2700
gtgaccgatt ggtagctcca ccccaactcc cttctgctgg gtggaatgca ggagctagct    2760
gcctccaact cactgtgacc tcagaaaaat gcctttatta ctcgggcctc agtttcctcg    2820
tctttaagta aggggcttgg atgagatgat tcaggaccc tttccaataa taaaatactg     2880
tgactgccaa aaaaaaaaaa aaaaaaaaaa aaaaaaaaaa aaaaaaaaaa aaaaaaaaaa    2940
aaaaaaaaaa aaaaaaaaaa aaaaaaaaaa aaaaaaaaaa aaaaaaaaaa aaaaaaaaaa    3000
aa                                                                  3002

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:  Novel
      Sequence

<400> SEQUENCE: 6
aaaacgccaa gagattgayg ctgtagc                                          27

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence:  Novel
      Sequence

<400> SEQUENCE: 7
ccccactgcc tcctccactg atgctc                                       26

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:  Novel
      Sequence

<400> SEQUENCE: 8
cagagatcta gcgaaccggg aaagggagac                                       30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:  Novel
```

```
                                    Sequence

<400> SEQUENCE: 9
tgcagatctc taacctgagt ctacagccag                                      30

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence:  Novel
      Sequence

<400> SEQUENCE: 10
aagaattcaa aacgccaaga gattgatgct gtagc                                35

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:  Novel
      Sequence

<400> SEQUENCE: 11
aagcggccgc taacctgagt ctacagccag                                      30

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence:  Novel
      Sequence

<400> SEQUENCE: 12
aaggatccat gagcgaaccg ggaaaggg                                        28

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence:  Novel
      Sequence

<400> SEQUENCE: 13
aaggatccct aacctgagtc tacagccag                                       29
```

HUMAN HOMOLOGUE OF THE DBF4/ASK1 PROTEIN, NUCLEIC ACIDS, AND METHODS RELATED TO THE SAME

This application is a continuation in part of the U.S. application Ser. No. 09/595,683 filed Jun. 16, 2000, now abandoned.

FIELD OF THE INVENTION

The present invention is directed, in part, to nucleic acid molecules encoding a novel human homologue of the DBF4/ASK1 protein (for "Activator of S phase Kinase"). This novel protein has been named DRF1 (from DBF4 Related Factor 1) and will be referred to herein with this term. The present invention is also directed to novel polypeptides, and assays for screening compounds which bind to DRF1 and/or modulate the activity of DRF1, and DRF1 associated complexes.

BACKGROUND OF THE INVENTION

DNA Replication Initiation and Role of the CDC7/DBF4 Kinase.

In eukaryotes, DNA replication is strictly regulated during cell cycle, occurring once and only once during S phase (Stillman, Science 274, 1659-1664 (1996)). A number of factors conserved in wide varieties of eukaryotes are known to play crucial roles in initiation and elongation stages of DNA replication. These include ORC (Origin Recognition Complex), MCM (Minichromosome Maintenance), Cdc6, Cdc45, RPA (Single-stranded DNA binding proteins), and DNA polymerases. Although assembly of a prereplicative complex (preRC) at an origin, which involves actions of ORC, Cdc6 and MCM proteins, is prerequisite for initiation of DNA replication (Diffley et al., Cell 78, 303-316. (1994); Newlon, Cell 91, 717-720. (1997)), such assembyly is not by itself sufficient for triggering DNA synthesis. Genetic evidence from budding yeast Saccharomyces cerevisiae has indicated that initiation of DNA replication requires action of the serine/threonine CDC7-DBF4 kinase. Molecular studies have now demonstrated that the CDC7/DBF4 kinase has a direct role in DNA replication origin firing.

This evidence is summarised below:
1) Temperature sensitive cdc7 and dbf4 mutant strains arrest with G1 DNA content after shift to restrictive temperature (Bousset, (1998), [published erratum appears in Genes Dev 1998 Apr 1;12(7):1072]. Genes Dev 12, 480-490).
2) CDC7 activity is required throughout S phase for origin firing; it is therefore not just a molecular switch between G1 and S. i.e. it is required for firing of early and late origins (Bousset et al., supra; Donaldson et al., (1998), Genes Dev 12, 491-501).
3) The DBF4 protein is recruited to origin DNA sequences in vivo (Dowell et al., (1994), [see comments], Science 265, 1243-1246).
4) CDC7/DBF4 kinase preferentially phoshorylates MCM proteins, a component of pre-replicative complexes bound at origins (Sato et al., (1997), EMBO J 16, 4340-4351; Lei et al., (1997), Genes Dev 11, 3365-3374.).
5) This phosphorylation is very likely to be important since a very specific mutation in the MCM5 gene was found to bypass the CDC7/DBF4 kinase requirement (Hardy et al, (1997), Proc Natl Acad Sci USA 94, 3151-3155).

Recently the presence of kinase complexes related to budding yeast Cdc7-Dbf4 has been demonstrated in other eukaryotic organisms including fission yeast, Xenopus and mammals (Masai et al., EMBO J 14, 3094-3104 (1995); Sato et al., EMBO J 16, 4340-4351 (1997); Kim et al., J Biol Chem 273, 23248-23257. (1998); Jiang et al., Proc. Natl. Acad. Sci. USA 94, 14320-14325. (1997); Hess et al., (1998); Gene 211, 133-140; Kumagai et al., Mol. Cell. Biol. 19, 5083-5095. (1999)).

Role of human CDC7/DBF4 complex in DNA replication was assessed using antibody microinjection approach. First, microinjection of specific anti-CDC7 antibody inhibits DNA synthesis in human tumor cells (Jiang et al., EMBO J 18, 5703-5713. (1999)) Secondly, two independent anti-DBF4 antibodies inhibited DNA synthesis when injected into human primary fibroblast KD cells (Kumagai et al., Mol. Cell. Biol. 19, 5083-5095. (1999)). The DNA replication was restored when the antigen was coinjected with antibody. Taken together, mammalian CDC7-related kinase complexes play pivotal roles in cell cycle progression, most likely in S phase initiation, as was discovered in yeast.

Human CDC7/DBF4 Genes and Proteins.

The human full length cDNA encoding for CDC7 kinase homologue was cloned by three different groups:
1) Sato et al. from Tokyo University, Japan, EMBO J 16, 4340-4351. (1997)).
2) Jiang et al. from Salk Institute USA, Proc. Natl. Acad. Sci. USA 94, 14320-14325. (1997).
3) Hess et al. from Pharmacia & Upjohn, Kalamazoo, USA, (1998), Gene 211, 133-140.

The cDNA encoding the human DBF4 subunit was first published in July 1999 by Kumagai et al., Mol. Cell. Biol. 19, 5083-5095. (1999), and more recently by Jiang et al., EMBO J. 18, 5703-5713. (1999).

The CDC7/DBF4 kinase, like cyclin-dependent kinases, is composed by a catalytic subunit CDC7 and a regulatory subunit DBF4, the latter also called ASK1 (activator of S phase kinase) (Kumagai et al., Mol. Cell. Biol. 19, 5083-5095. (1999)). Kinase activity is dependent upon physical interaction between the two subunits, the CDC7 protein alone does not show kinase activity (Kumagai et al., Mol. Cell. Biol. 19, 5083-5095. (1999); Jiang et al., EMBO J 18, 5703-5713. (1999)).

Kinase activity fluctuates during the cell cycle. Since CDC7 levels are constant, this fluctuation might reflect the available amount of activator protein (Kumagai et al., Mol. Cell. Biol. 19, 5083-5095. (1999); Jiang et al., EMBO J 18, 5703-5713. (1999)). No other mechanisms that could regulate the activity of the enzyme have been observed to date but cannot be excluded.

CDC7 is a 574-aminoacid polypeptide that shares a strong homology with S. cerevisiae CDC7 protein (Sato et al., EMBO J 16, 4340-4351. (1997); Jiang et al., Proc. Natl. Acad. Sci. USA 94, 14320-14325. (1997); Hess et al., (1998), Gene 211, 133-140). DBF4 protein has a very limited sequence homology with the yeast counterpart. This homology is confined in two boxes called ASK motive-N (N-terminal) and ASK motif-C (C-terminal). The role of these boxes is not clear although the motif-C is within the interaction domain with CDC7 (Kumagai et al., Mol. Cell. Biol. 19, 5083-5095. (1999)). At present time these two boxes appear to be a unique feature of DBF4 related proteins. Because of the importance of CDC7/DBF4 proteins in DNA replication process it is important to identify genes and proteins with related function or structure and that might regulate activity of CDC7 kinase itself.

The present invention involves the surprising discovery of a novel polypeptide, herein designated DRF1, that exhibits a functional homology to human DBF4/ASK1, and its role as a key component, for example, in regulating CDC7 kinase activity. DRF1 is, thus, useful in the search for novel agents that can modify and/or control DRF1 and/or CDC7 kinase activity. These and other aspects of the invention are described below.

SUMMARY OF THE INVENTION

The present invention is directed to, in part, isolated nucleic acid molecules comprising SEQ ID NO:1, or a fragment thereof; SEQ ID NO:2, or a fragment thereof; a nucleotide sequence complementary to at least a portion of SEQ ID NO:1 or SEQ ID NO:2; a nucleotide sequence homologous to SEQ ID NO:1 or SEQ ID NO:2, or a fragment thereof; a nucleotide sequence that encodes a polypeptide comprising SEQ ID NO:3, or a fragment thereof; or a nucleotide sequence that encodes a polypeptide comprising an amino acid sequence homologous to SEQ ID NO:3, or a fragment thereof.

The present invention is also directed to recombinant expression vectors comprising any of the nucleic acid molecules described above.

The present invention is also directed to host cells transformed with a recombinant expression vector comprising any of the nucleic acid molecules described above.

The present invention is also directed to methods of producing a polypeptide comprising SEQ ID NO:3, or a homolog or fragment thereof, by introducing a recombinant expression vector comprising any of the nucleic acid molecules described above into a compatible host cell, growing the host cell under conditions suitable for expression of the polypeptide, and recovering the polypeptide from the host cell.

The present invention is also directed to compositions comprising any of the nucleic acid molecules described above and an acceptable carrier or diluent.

The present invention is also directed to isolated polypeptides encoded by any of the nucleic acid molecules described above.

The present invention is also directed to compositions comprising a polypeptide encoded by any of the nucleic acid molecules described above and an acceptable carrier or diluent.

The present invention is also directed to isolated antibodies which bind to an epitope on a polypeptide encoded by any of the nucleic acid molecules described above.

The present invention is also directed to kits comprising antibodies which bind to a polypeptide encoded by any of the nucleic acid molecules described above and a negative control antibody.

The present invention is also directed to methods of inducing an immune response in a mammal against a polypeptide encoded by any of the nucleic acid molecules described above by administering to the mammal an amount of the polypeptide sufficient to induce the immune response.

The present invention is also directed to methods of identifying a compound which binds to DRF1 or to a DRF1-containing complex, by contacting DRF1 or DRF1-containing complex with a compound, and determining whether the compound binds DRF1 or DRF1-containing complex.

The present invention is also directed to methods of identifying a compound which binds a nucleic acid molecule encoding DRF1 or DRF1-containing complex by contacting a nucleic acid molecule encoding DRF1 or DRF1-containing complex with a compound, and determining whether the compound binds the nucleic acid molecule.

The present invention is also directed to methods of identifying a compound which modulates the activity of DRF1 or of DRF1-containing complex by contacting DRF1 or DRF1-containing complex with a compound, and determining whether DRF1 or DRF1-containing complex activity is modified.

The present invention is also directed to compounds which modulate DRF1 or DRF1-containing complex activity identified by contacting DRF1 or DRF1-containing complex with the compound, and determining whether the compound modifies activity of DRF1 or DRF1-containing complex, binds to DRF1 or DRF1-containing complex, or binds to a nucleic acid molecule encoding DRF1 or DRF1-containing complex.

These and other aspects of the invention are described in greater detail below.

DETAILED DESCRIPTION OF PREFERRED EMBODIMENTS

The present invention provides, inter alia, isolated and purified polynucleotides that encode DRF1 or a portion thereof, vectors containing these polynucleotides, host cells transformed with these vectors, processes of mailing DRF1, methods of using the above polynucleotides and vectors, isolated and purified DRF1, and methods of screening compounds which modulate DRF1 activity.

Various definitions are made throughout this document. Most words have the meaning that would be attributed to those words by one skilled in the art. Words specifically defined either below or elsewhere in this document have the meaning provided in the context of the present invention as a whole and as are typically understood by those skilled in the art.

As used herein, the term "activity" refers to a variety of measurable indicia suggesting or revealing binding, either direct or indirect; affecting a response, i.e. having a measurable affect in response to some exposure or stimulus, including, for example, the affinity of a compound for directly binding a polypeptide or polynucleotide of the invention, or, for example, measurement of amounts of upstream or downstream proteins or other similar functions after some stimulus or event.

As used herein, the abbreviation in lower case drf1 refers to a gene, cDNA, RNA or nucleic acid sequence while the upper case version DRF1 refers to a protein, polypeptide, peptide, oligopeptide, or amino acid sequence.

As used herein, the term "antibody" is meant to refer to complete, intact antibodies, and Fab fragments and $F(ab)_2$ fragments thereof. Complete, intact antibodies include monoclonal antibodies such as murine monoclonal antibodies, chimeric antibodies and humanized antibodies.

As used herein, the term "binding" means the physical or chemical interaction between two proteins or compounds or associated proteins or compounds or combinations thereof. Binding includes ionic, non-ionic, Hydrogen bonds, Van der Waals, hydrophobic interactions, etc. The physical interaction, the binding, can be either direct or indirect, indirect being through or due to the effects of another protein or compound. Direct binding refers to interactions that do not take place through or due to the effect of another protein or compound but instead are without other substantial chemical intermediates.

As used herein, the term "compound" means any identifiable chemical or molecule, including, but not limited to, small molecule, peptide, protein, sugar, nucleotide, or nucleic acid, and such compound can be natural or synthetic.

As used herein, the term "complementary" refers to Watson-Crick basepairing between nucleotide units of a nucleic acid molecule.

As used herein, the term "contacting" means bringing together, either directly or indirectly, a compound into physical proximity to a polypeptide or polynucleotide of the invention. The polypeptide or polynucleotide can be in any number of buffers, salts, solutions etc. Contacting includes, for example, placing the compound into a beaker, microtiter plate, cell culture flask, or a microarray, such as a gene chip, or the like, which contains the nucleic acid molecule, or polypeptide encoding the DRF1 or fragment thereof.

As used herein, the phrase "homologous nucleotide sequence," or "homologous amino acid sequence," or variations thereof, refers to sequences characterised by a homology, at the nucleotide level or amino acid level, of at least about 60%, more preferably at least about 70%, more preferably at least about 80%, more preferably at least about 90%, and most preferably at least about 95% to the entire SEQ ID NO:1 or SEQ ID NO:2, or to at least a portion of SEQ ID NO: 1 or SEQ ID NO:2 which encodes a functional domain of the encoded polypeptide, or to SEQ ID NO:3. Homologous nucleotide sequences include those sequences coding for isoforms of DRF1 proteins. Such isoforms can be expressed in different tissues of the same organism as a result of, for example, alternative splicing of RNA. Alternatively, isoforms can be encoded by different genes. Homologous nucleotide sequences include nucleotide sequences encoding for a DRF1 protein of species other than humans, including, but not limited to, mammals. Homologous nucleotide sequences also include, but are not limited to, naturally occurring allelic variations and mutations of the nucleotide sequences set forth herein. A homologous nucleotide sequence does not, however, include the nucleotide sequence encoding DBF4/ASK1. Homologous amino acid sequences include those amino acid sequences which encode conservative amino acid substitutions in SEQ ID NO:3, as well as polypeptides having CDC7 kinase activating activity. A homologous amino acid sequence does not, however, include the amino acid sequence of DBF4/ASK1. Percent homology can be determined by, for example, the Gap program (Wisconsin Sequence Analysis Package, Version 8 for Unix, Genetics Computer Group, University Research Park, Madison Wis.), using the default settings, which uses the algorithm of Smith and Waterman (*Adv. Appl. Math.,* 1981, 2, 482-489, which is incorporated herein by reference in its entirety).

As used herein, the term "isolated" nucleic acid molecule refers to a nucleic acid molecule (DNA or RNA) that has been removed from its native environment. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules.

As used herein, the terms "modulates" or "modifies" means an increase or decrease in the amount, quality, or effect of a particular activity or protein.

As used herein, the term "oligonucleotide" refers to a series of linked nucleotide residues which has a sufficient number of bases to be used in a polymerase chain reaction (PCR). This short sequence is based on (or designed from) a genomic or cDNA sequence and is used to amplify, confirm, or reveal the presence of an identical, similar or complementary DNA or RNA in a particular cell or tissue. Oligonucleotides comprise portions of a DNA sequence having at least about 10 nucleotides and as many as about 50 nucleotides, preferably about 15 to 30 nucleotides. They are chemically synthesized and may be used as probes.

As used herein, the term "probe" refers to nucleic acid sequences of variable length, preferably between at least about 10 and as many as about 6,000 nucleotides, depending on use. They are used in the detection of identical, similar, or complementary nucleic acid sequences. Longer length probes are usually obtained from a natural or recombinant source, are highly specific and much slower to hybridize than oligomers. They may be single- or double-stranded and carefully designed to have specificity in PCR, hybridization membrane-based, or ELISA-like technologies.

As used herein, the phrase "stringent hybridization conditions" or "stringent conditions" refers to conditions under which a probe, primer, or oligonucleotide will hybridize to its target sequence, but to no other sequences. Stringent conditions are sequence-dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target sequence hybridize to the target sequence at equilibrium. Since the target sequences are generally present in excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g. 10 to 50 nucleotides) and at least about 60° C. for longer probes, primers or oligonucleotides. Stringent conditions may also be achieved with the addition of destabilising agents, such as formamide.

The amino acid sequences are presented in the amino to carboxy direction, from left to right. The amino and carboxy groups are not presented in the sequence. The nucleotide sequences are presented by single strand only, in the 5' to 3' direction, from left to right. Nucleotides and amino acids are represented in the manner recommended by the IUPAC-IUB Biochemical Nomenclature Commission, or (for amino acids) by three letters code.

One aspect of the present invention is directed to nucleic acid molecules comprising novel nucleotide sequences encoding DRF1. The nucleic acid molecules are preferably either RNA or DNA, but may contain both RNA and DNA monomers or peptide nucleic acid monomers. The nucleic acid molecule may be single stranded or double stranded. The monomers of the nucleic acid molecules may be linked via conventional phosphodiester bonds or modified bonds, such as, for example, phosphorothioate bonds and the like. In addition, the sugar moieties of the monomers may be modified by, for example, addition of 2' substitutions which help confer nuclease resistance and/or cellular uptake.

In a preferred embodiment of the invention, the nucleic acid molecule comprises SEQ ID NO:1, which is 3006 bases in length and comprises an open reading frame (ORF) of approximately 1845 nucleotides (from about position 139 to about position 1983 within SEQ ID NO:1) which encodes DRF1. A comparison between human dbf4/ask1 cDNA and drf1 cDNA of SEQ ID NO:1 displayed an overall sequence homology (identical residues) of 42.8%.

Alternatively, the nucleic acid molecule comprises a fragment of SEQ ID NO:1. Preferably, the fragment comprises from about 10 to about 100 nucleotides, from about 101 to about 200 nucleotides, from about 201 to about 300 nucleotides, from about 301 to about 400 nucleotides, from about 401 to about 500 nucleotides, from about 501 to about 600 nucleotides, from about 601 to about 700 nucleotides, from about 701 to about 800 nucleotides, from about 801 to about 900 nucleotides, from about 901 to about 1000 nucleotides, from about 1001 to about 1100 nucleotides, from about 1101 to about 1200 nucleotides, from about 1201 to about 1300 nucleotides, from about 1301 to about 1400 nucleotides, from about 1401 to about 1500 nucleotides, from about 1501 to about 1600 nucleotides, from about 1601 to about 1700 nucleotides, from about 1701 to about 1800 nucleotides, from about 1801 to about 1900 nucleotides, from about 1901 to about 2000 nucleotides, from about 2001 to about 2100 nucleotides, from about 2101 to about 2200 nucleotides, from about 2201 to about 2300 nucleotides, from about 2301 to about 2400 nucleotides, from about 2401 to about 2500 nucleotides, from about 2501 to about 2600 nucleotides, from about 2601 to about 2700 nucleotides, from about 2701 to about 2800 nucleotides, from about 2801 to about 2900 nucleotides, from about 2901 to about 3000 nucleotides, from about 3001 to about 3006 ucleotides, and any combinations thereof. The fragment can be located within any portion of SEQ ID NO:1.

In another preferred embodiment of the invention, the nucleic acid molecule comprises SEQ ID NO:2, which is 1845 bases in length and comprises the ORF (from about position 139 to about position 1983 within SEQ ID NO:1) described above. Alternatively, the nucleic acid molecule comprises a fragment of SEQ ID NO:2. Preferably, the fragment comprises from about 10 to about 100 nucleotides, from about 101 to about 200 nucleotides, from about 201 to about 300 nucleotides, from about 301 to about 400 nucleotides, from about 401 to about 500 nucleotides, from about 501 to about 600 nucleotides, from about 601 to about 700 nucleotides, from about 701 to about 800 nucleotides, from about 801 to about 900 nucleotides, from about 901 to about 1000 nucleotides, from about 1001 to about 1100 nucleotides, from about 1101 to about 1200 nucleotides, from about 1201 to about 1300 nucleotides, from about 1301 to about 1400 nucleotides, from about 1401 to about 1500 nucleotides, from about 1501 to about 1600 nucleotides, from about 1601 to about 1700 nucleotides, from about 1701 to about 1800 nucleotides, from about 1801 to about 1845 nucleotides, and any combinations thereof. The fragment can be located within any portion of SEQ ID NO:2.

In another preferred embodiment of the invention, the nucleic acid molecule comprises a nucleotide sequence complementary to at least a portion of SEQ ID NO:1 or SEQ ID NO:2. Preferably, the nucleic acid molecule comprises a nucleotide sequence complementary to the entire sequence recited in SEQ ID NO:1 or SEQ ID NO:2. Alternatively, the nucleic acid molecule comprises a nucleotide sequence complementary to a portion of SEQ ID NO:1 or SEQ ID NO:2 (i.e., complementary to any of the fragments described above). Nucleotide sequences complementary to at least a portion of SEQ ID NO:1 or SEQ ID NO:2 include, for example, oligonucleotides which hybridize under stringent hybridization conditions to at least a portion of SEQ ID NO:1 or SEQ ID NO:2. Preferred oligonucleotides comprise at least about 10 nucleotides and as many as about 50 nucleotides, preferably about 15 to 30 nucleotides. They are chemically synthesised and can be used as probes, primers, and as antisense agents.

In another preferred embodiment of the invention, the nucleic acid molecule comprises a nucleotide sequence homologous to SEQ ID NO:1 or SEQ ID NO:2. Preferably, the nucleotide sequence is at least about 60% homologous, more preferably at least about 70% homologous, more preferably at least about 80% homologous, more preferably at least about 90% homologous, and most preferably at least about 95% homologous to the entire SEQ ID NO:1 or SEQ ID NO:2. Alternatively, the nucleotide sequence is at least about 60% homologous, more preferably at least about 70% homologous, more preferably at least about 80% homologous, more preferably at least about 90% homologous, and most preferably at least about 95% homologous to a portion of SEQ ID NO:1 or SEQ ID NO:2 which encodes a functional domain of the polypeptide encoded thereby. In addition, a nucleotide sequence homologous to SEQ ID NO:1 or SEQ ID NO:2 also includes a fragment of the nucleotide sequence homologous to SEQ ID NO:1 or SEQ ID NO:2 of the lengths described above. A homologous nucleotide sequence does not, however, include the nucleotide sequence encoding DBF4/ASK1.

In another preferred embodiment of the invention, the nucleic acid molecule comprises a nucleotide sequence that encodes a polypeptide comprising SEQ ID NO:3. The nucleic acid molecule preferably comprises SEQ ID NO:2 or comprises SEQ ID NO:2 containing codon substitutions which reflect the degeneracy of the genetic code. As is well known in the art, because of the degeneracy of the genetic code, there are numerous other DNA and RNA molecules that can code for the same polypeptide as that encoded by SEQ ID NO:2. The present invention, therefore, contemplates these other DNA and RNA molecules which, on expression, encode the polypeptide of SEQ ID NO:3. DNA and RNA molecules other than those specifically disclosed herein characterised simply by a change in a codon for a particular amino acid, are within the scope of the present invention.

As is well known in the art, because of the degeneracy of the genetic code, there are numerous other DNA and RNA molecules that can code for the same polypeptide as that encoded by the aforementioned drf1 gene. The present invention, therefore, contemplates those other DNA and RNA molecules which, on expression, encode the polypeptide of SEQ ID NO: 3. Having identified the amino acid residue sequence encoded by a drf1 gene, and with knowledge of all triplet codons for each particular amino acid residue, it is possible to describe all such encoding RNA and DNA sequences. DNA and RNA molecules other than those specifically disclosed herein characterised simply by a change in a codon for a particular amino acid, are within the scope of this invention.

A table of amino acids and their representative abbreviations, symbols and codons is set forth below in the following Table 1.

TABLE 1

| Amino acid | Abbrev. | Symbol | Codon(s) |
|---|---|---|---|
| Alanine | Ala | A | GCA GCC GCG GCU |
| Cysteine | Cys | C | UGA UGU |
| Aspartic acid | Asp | D | GAC GAU |
| Glutamic acid | Glu | E | GAA GAG |

TABLE 1-continued

| Amino acid | Abbrev. | Symbol | Codon(s) |
|---|---|---|---|
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

As is well known in the art, codons constitute triplet sequences of nucleotides in mRNA molecules and, as such, are characterised by the base uracil (U) in place of base thymidine (T) (which is present in DNA molecules). A simple change in a codon for the same amino acid residue within a polynucleotide will not change the sequence or structure of the encoded polypeptide.

Alternatively, the nucleic acid molecule comprises a nucleotide sequence that encodes a fragment of the polypeptide encoding SEQ ID NO:3. Preferably, the fragment comprises from about 5 to about 20 amino acids, from about 21 to about 40 amino acids, from about 41 to about 60 amino acids, from about 61 to about 80 amino acids, from about 81 to about 100 amino acids, from about 101 to about 120 amino acids, from about 121 to about 140 amino acids, from about 141 to about 160 amino acids, from about 161 to about 180 amino acids, from about 181 to about 200 amino acids, from about 201 to about 220 amino acids, from about 221 to about 240 amino acids, from about 241 to about 260 amino acids, from about 261 to about 280 amino acids, from about 281 to about 300 amino acids, from about 301 to about 320 amino acids, from about 321 to about 340 amino acids, from about 341 to about 360 amino acids, from about 361 to about 380 amino acids, from about 381 to about 400 amino acids, from about 401 to about 420 amino acids, from about 421 to about 440 amino acids, from about 441 to about 460 amino acids, from about 461 to about 480 amino acids, from about 481 to about 500 amino acids, from about 501 to about 520 amino acids, from about 521 to about 540 amino acids, from about 541 to about 560 amino acids, from about 561 to about 580 amino acids, from about 581 to about 600 amino acids, from about 601 to about 610 amino acids, and any combinations thereof. The fragment can be located within any portion of SEQ ID NO:3.

In another preferred embodiment of the invention, the nucleic acid molecule comprises a nucleotide sequence that encodes a polypeptide comprising an amino acid sequence homologous to SEQ ID NO:3. Alternatively, the nucleic acid molecule comprises a nucleotide sequence that encodes a fragment of the polypeptide comprising an amino acid sequence homologous to SEQ ID NO:3. Preferably, the fragment comprises from about 5 to about 20 amino acids, from about 21 to about 40 amino acids, from about 41 to about 60 amino acids, from about 61 to about 80 amino acids, from about 81 to about 100 amino acids, from about 101 to about 120 amino acids, from about 121 to about 140 amino acids, from about 141 to about 160 amino acids, from about 161 to about 180 amino acids, from about 181 to about 200 amino acids, from about 201 to about 220 amino acids, from about 221 to about 240 amino acids, from about 241 to about 260 amino acids, from about 261 to about 280 amino acids, from about 281 to about 300 amino acids, from about 301 to about 320 amino acids, from about 321 to about 340 amino acids, from about 341 to about 360 amino acids, from about 361 to about 380 amino acids, from about 381 to about 400 amino acids, from about 401 to about 420 amino acids, from about 421 to about 440 amino acids, from about 441 to about 460 amino acids, from about 461 to about 480 amino acids, from about 481 to about 500 amino acids, from about 501 to about 520 amino acids, from about 521 to about 540 amino acids, from about 541 to about 560 amino acids, from about 561 to about 580 amino acids, from about 581 to about 600 amino acids, from about 601 to about 610 amino acids, and any combinations thereof. The fragment can be located within any portion of SEQ ID NO:3.

With the knowledge of the nucleotide sequence information disclosed in the present invention, one skilled in the art can identify and obtain nucleotide sequences which encode DRF1 from different sources (i.e., different tissues or different organisms) through a variety of means well known to the skilled artisan and disclosed by, for example, Sambrook et al., "Molecular cloning: a laboratory manual", Second Edition, Cold Spring Harbor Press, Cold Spring Harbor, N.Y. (1989), which is incorporated herein by reference in its entirety.

For example, DNA which encodes DRF1 may be obtained by screening of mRNA, cDNA, or genomic DNA with oligonucleotide probes generated from the drf1 gene sequence information provided herein. Probes may be labeled with a detectable group, such as a fluorescent group, a radioactive atom or a chemiluminescent group in accordance with procedures known to the skilled artisan and used in conventional hybridization assays, as described by, for example, Sambrook et al.

A nucleic acid molecule comprising any of the drf1 nucleotide sequences described above can alternatively be recovered by use of the polymerase chain reaction (PCR) procedure, with the PCR oligonucleotide primers produced from the nucleotide sequences provided herein. See U.S. Pat. Nos. 4,683,195 to Mullis et al. and 4,683,202 to Mullis. The PCR reaction provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotides probes to serve as primers for the template-dependent, polymerase mediated replication of a desired nucleic acid molecule.

A wide variety of alternative cloning and in vitro amplification methodologies are well known to those skilled in the art. Examples of these techniques are found in, for example, Berger et al., *Guide to Molecular Cloning Techniques*, Methods in Enzymology 152 Academic Press, Inc., San Diego, Calif. (Berger), which is incorporated herein by reference in its entirety.

The nucleic acid molecules of the present invention, and fragments derived therefrom, are useful for screening for restriction fragment length polymorphism (RFLP) associated with certain disorders, as well as for genetic mapping.

Antisense oligonucleotides, or fragments of SEQ ID NO:1 or SEQ ID NO:2, or sequences complementary thereto, derived from the nucleotide sequences of the present invention encoding DRF1 are useful as diagnostic tools for probing gene expression in various tissues. For example, tissue can be probed in situ with oligonucleotide probes carrying detectable groups by conventional autoradiography techniques to investigate native expression of this enzyme or pathological conditions relating thereto. Antisense oligonucleotides are preferably directed to regulatory regions of SEQ ID NO:1 or SEQ ID NO:2 or mRNA corresponding thereto, including, but not limited to, the initiation codon, TATA box, enhancer sequences, and the like.

Automated sequencing methods were used to obtain or verify the nucleotide sequence of drf1. The drf1 nucleotide sequences of the present invention were obtained for both DNA strands, and are believed to be 100% accurate. However, as is known in the art, nucleotide sequence obtained by automated methods may contain some errors. Nucleotide sequences determined by automation are typically at least about 90%, more typically at least about 95% to at least about 99.9% identical to the actual nucleotide sequence of a given nucleic acid molecule. The actual sequence may be more precisely determined using manual sequencing methods, which are well known in the art. An error in sequence which results in an insertion or deletion of one or more nucleotides may result in a frame shift in translation such that the predicted amino acid sequence will differ from that which would be predicted from the actual nucleotide sequence of the nucleic acid molecule, starting at the point of the mutation.

Another aspect of the present invention is directed to vectors, or recombinant expression vectors, comprising any of the nucleic acid molecules described above. Vectors are used herein either to amplify DNA or RNA encoding DRF1 and/or to express DNA which encodes DRF1. Preferred vectors include, but are not limited to, plasmids, phages, cosmids, episomes, viral particles or viruses, and integratable DNA fragments (i.e., fragments integratable into the host genome by homologous recombination). Preferred viral particles include, but are not Limited to, adenoviruses, parvoviruses, herpesviruses, poxviruses, adeno-associated viruses, Semliki Forest viruses, vaccinia viruses, and retroviruses. Preferred expression vectors include, but are not limited to, pcDNA3 (Invitrogen) and pSVL (Pharmacia Biotech). Other expression vectors include, but are not limited to, pSPORT vectors, pGEM vectors (Promega), pPROEXvectors (LTI, Bethesda, Md.), Bluescript vectors (Stratagene), pQE vectors (Qiagen), pSE420 (Invitrogen), and pYES2 (Invitrogen) and the range of Gateway expression plasmids (LifeTechnologies).

Preferred expression vectors are replicable DNA constructs in which a DNA sequence encoding DRF1 is operably linked to suitable control sequences capable of effecting the expression of the DRF1 in a suitable host. DNA regions are operably linked when they are functionally related to each other. For example, a promoter is operably linked to a coding sequence if it controls the transcription of the sequence. Amplification vectors do not require expression control domains, but rather need only the ability to replicate in a host, usually conferred by an origin of replication, and a selection gene to facilitate recognition of transformants. The need for control sequences into the expression vector will vary depending upon the host selected and the transformation method chosen. Generally, control sequences include a transcriptional promoter, an optional operator sequence to control transcription, a sequence encoding suitable mRNA ribosomal binding, and sequences which control the termination of transcription and translation.

Preferred vectors preferably contain a promoter which is recognised by the host organism. The promoter sequences of the present invention may be either prokaryotic, eukaryotic or viral. Examples of suitable prokaryotic sequences include the $P_R$ and $P_L$ promoters of bacteriophage lambda (The bacteriophage Lambda, Hershey, A. D., Ed., Cold Spring Harbor Press, Cold Spring Harbor, N.Y. (1973), which is incorporated herein by reference in its entirety; Lambda II, Hendrix, R. W., Ed., Cold Spring Harbor Press, Cold Spring Harbor, N.Y. (1980), which is incorporated herein by reference in its entirety); the trp, recA, heat shock, and lacZ promoters of *E. coli* and the SV40 early promoter (Benoist, et al. *Nature,* 1981, 290, 304-310, which is incorporated herein by reference in its entirety). Additional promoters include, but are not limited to, mouse mammary tumor virus, long terminal repeat of human immunodeficiency virus, maloney virus, cytomegalovirus immediate early promoter, Epstein Barr virus, rous sarcoma virus, human actin, human myosin, human hemoglobin, human muscle creatine, and human metalothionein.

Additional regulatory sequences can also be included in preferred vectors. Preferred examples of suitable regulatory sequences are represented by the Shine-Dalgarno of the replicase gene of the phage MS-2 and of the gene cII of bacteriophage lambda. The Shine-Dalgarno sequence may be directly followed by the DNA encoding DRF1 and result in the expression of the mature DRF1 protein.

Moreover, suitable expression vectors can include an appropriate marker which allows the screening of the transformed host cells. The transformation of the selected host is carried out using any one of the various techniques well known to the expert in the art and described in Sambrook et al., supra.

An origin of replication can also be provided either by construction of the vector to include an exogenous origin or may be provided by the host cell chromosomal replication mechanism. If the vector is integrated into the host cell chromosome, the latter may be sufficient. Alternatively, rather than using vectors which contain viral origins of replication, one skilled in the art can transform mammalian cells by the method of co-transformation with a selectable marker and DRF1 DNA. An example of a suitable marker is dihydrofolate reductase (DHFR) or thymidine kinase (see, U.S. Pat. No. 4,399,216).

Nucleotide sequences encoding DRF1 may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesiderable joining, and ligation with appropriate ligases. Techniques for such manipulation are disclosed by Sambrook et al., supra and are well known in the art. Methods for construction of mammalian expression vectors are disclosed in, for example, Okayama et al., *Mol. Cell. Biol.,* 1983, 3, 280, Cosman et al., *Mol. Immunol.,* 1986, 23, 935, Cosman et al.,

*Nature*, 1984, 312, 768, EP-A-0367566, and WO 91/18982, each of which is incorporated herein by reference in its entirety.

Another aspect of the present invention is directed to transformed host cells having an expression vector comprising any of the nucleic acid molecules described above. Expression of the nucleotide sequence occurs when the expression vector is introduced into an appropriate host cell. Suitable host cells for expression of the polypeptides of the invention include, but are not limited to, prokaryotes, yeast, and eukaryotes. If a prokaryotic expression vector is employed, then the appropriate host cell would be any prokaryotic cell capable of expressing the cloned sequences. Suitable prokaryotic cells include, but are not limited to, bacteria of the genera *Escherichia, Bacillus, Salmonella, Pseudomonas, Streptomyces*, and *Staphylococcus*.

If a eukaryotic expression vector is employed, then the appropriate host cell would be any eukaryotic cell capable of expressing the cloned sequence. Preferably, eukaryotic cells are cells of higher eukaryotes. Suitable eukaryotic cells include, but are not limited to, non-human mammalian tissue culture cells and human tissue culture cells. Preferred host cells include, but are not limited to, insect cells, HeLa cells, Chinese hamster ovary cells (CHO cells), African green monkey kidney cells (COS cells), human 293 cells, and murine 3T3 fibroblasts. Propagation of such cells in cell culture has become a routine procedure (see, Tissue Culture, Academic Press, Kruse and Patterson, eds. (1973), which is incorporated herein by reference in its entirety).

In addition, a yeast host may be employed as a host cell. Preferred yeast cells include, but are not limited to, the genera *Saccharomyces, Pichia,* and *Kluveromyces*. Preferred yeast hosts are *S. cerevisiae* and *P. pastoris*. Preferred yeast vectors can contain an origin of replication sequence from a 2T yeast plasmid, an autonomously replication sequence (ARS), a promoter region, sequences for polyadenylation, sequences for transcription termination, and a selectable marker gene. Shuttle vectors for replication in both yeast and *E. coli* are also included herein.

Alternatively, insect cells may be used as host cells. In a preferred embodiment, the polypeptides of the invention are expressed using a baculovirus expression system (see, Luckow et al., *Bio/Technology*, 1988, 6, 47, Baculovirus Expression Vectors: A Laboratory Manual, O'Rielly et al. (Eds.), W. H. Freeman and Company, New York, 1992, and U.S. Pat. No. 4,879,236, each of which is incorporated herein by reference in its entirety). In addition, the MAX-BAC™ complete baculovirus expression system (Invitrogen) can, for example, be used for production in insect cells.

Another aspect of the present invention is directed to compositions, including pharmaceutical compositions, comprising any of the nucleic acid molecules or recombinant expression vectors described above and an acceptable carrier or diluent. Preferably, the carrier or diluent is pharmaceutically acceptable. Suitable carriers are described in the most recent edition of *Remington's Pharmaceutical Sciences*, A. Osol, a standard reference text in this field, which is incorporated herein by reference in its entirety. Preferred examples of such carriers or diluents include, but are not limited to, water, saline, Ringer's solution, dextrose solution, and 5% human serum albumin. Liposomes and non-aqueous vehicles such as fixed oils may also be used. The formulations are sterilized by commonly used techniques.

Another aspect of the present invention is directed to an isolated polypeptide encoded by a nucleic acid molecule described above. In preferred embodiments of the invention, the isolated polypeptide comprises the amino acid sequence set forth in SEQ ID NO:3. A comparison between human DBF4/ASK1 and DRF1 of SEQ ID NO:3 displayed an overall sequence homology (identical residues) of 22.1%.

Alternatively, the polypeptide is a fragment of the polypeptide encoding SEQ ID NO:3. Preferably, the fragment comprises from about 5 to about 20 amino acids, from about 21 to about 40 amino acids, from about 41 to about 60 amino acids, from about 61 to about 80 amino acids, from about 81 to about 100 amino acids, from about 101 to about 120 amino acids, from about 121 to about 140 amino acids, from about 141 to about 160 amino acids, from about 161 to about 180 amino acids, from about 181 to about 200 amino acids, from about 201 to about 220 amino acids, from about 221 to about 240 amino acids, from about 241 to about 260 amino acids, from about 261 to about 280 amino acids, from about 281 to about 300 amino acids, from about 301 to about 320 amino acids, from about 321 to about 340 amino acids, from about 341 to about 360 amino acids, from about 361 to about 380 amino acids, from about 381 to about 400 amino acids, from about 401 to about 420 amino acids, from about 421 to about 440 amino acids, from about 441 to about 460 amino acids, from about 461 to about 480 amino acids, from about 481 to about 500 amino acids, from about 501 to about 520 amino acids, from about 521 to about 540 amino acids, from about 541 to about 560 amino acids, from about 561 to about 580 amino acids, from about 581 to about 600 amino acids, from about 601 to about 610 amino acids, and any combinations thereof. The fragment can be located within any portion of SEQ ID NO:3.

In another preferred embodiment of the invention, the polypeptide comprises an amino acid sequence homologous to SEQ ID NO:3 or a fragment thereof as described above. It is to be understood that the present invention includes proteins homologous to, and having essentially the same biological properties as, the polypeptide encoded by the nucleotide sequences described herein, i.e., a variant. This definition is intended to encompass isoforms and natural allelic variants of the drf1 gene described herein. These variant forms may result from, for example, alternative splicing or differential expression in different tissue of the same source organism. The variant forms may be characterised by, for example, amino acid insertion(s), deletion(s) or substitution(s). In this connection, a variant form having an amino acid sequence which has at least about 70% sequence homology, at least about 80% sequence homology, preferably about 90% sequence homology, more preferably about 95% sequence homology and most preferably about 98% sequence homology to SEQ ID NO:3, is contemplated as being included in the present invention. A preferred homologous polypeptide comprises at least one conservative amino acid substitution compared to SEQ ID NO:3. Amino acid "insertions", "substitutions" or "deletions" are changes to or within an amino acid sequence. The variation allowed in a particular amino acid sequence may be experimentally determined by producing the peptide synthetically or by systematically making insertions, deletions, or substitutions of nucleotides in the drf1 sequence using recombinant DNA techniques.

Alterations of the naturally occurring amino acid sequence can be accomplished by any of a number of known techniques. For example, mutations can be introduced into the polynucleotide encoding a polypeptide at particular locations by procedures well known to the skilled artisan, such as oligonucleotide-directed mutagenesis, which is described by Walder et al., *Gene*, 1986, 42, 133, Bauer et al., *Gene*, 1985, 37, 73, Craik, BioTechniques, January 1985, pp.12-19, Smith et al., Genetic Engineering: Principles and Methods, Plenum Press (1981), and U.S. Pat. Nos. 4,518,584 and 4,737,462, each of which is incorporated herein by reference in its entirety.

Preferably, a DRF1 variant of the present invention will exhibit substantially the biological activity of a naturally occurring DRF1 polypeptide. By "exhibit substantially the biological activity of a naturally occurring DRF1 polypeptide" is meant that DRF1 variants within the scope of the invention can comprise conservatively substituted sequences, meaning that one or more amino acid residues of a DRF1 polypeptide are replaced by different residues that do not alter the secondary and/or tertiary structure of the DRF1 polypeptide. Such substitutions may include the replacement of an amino acid by a residue having similar physicochemical properties, such as substituting one aliphatic residue (Ile, Val, Leu or Ala) for another, or substitution between basic residues Lys and Arg, acidic residues Glu and Asp, amide residues Gln and Asn, hydroxyl residues Ser and Tyr, or aromatic residues Phe and Tyr. Further information regarding making phenotypically silent amino acid exchanges can be found in Bowie et al., *Science*, 1990, 247, 1306-1310, which is incorporated herein by reference in its entirety. Other DRF1 variants which might retain substantially the biological activities of DRF1 are those where amino acid substitutions have been made in areas outside functional regions of the protein.

The polypeptides to be expressed in such host cells may also be fusion proteins which include regions from heterologous proteins. Such regions may be included to allow, e.g., secretion, improved stability, or facilitated purification of the polypeptide. For example, a sequence encoding an appropriate signal peptide can be incorporated into expression vectors. A DNA sequence for a signal peptide (secretory leader) may be fused in-frame to the polynucleotide sequence so that the polypeptide is translated as a fusion protein comprising the signal peptide. A signal peptide that is functional in the intended host cell promotes extracellular secretion of the polypeptide. Preferably, the signal sequence will be cleaved from the polypeptide upon secretion of the polypeptide from the cell. Thus, preferred fusion proteins can be produced in which the N-terminus of DRF1 is fused to a carrier peptide.

In one embodiment, the polypeptide comprises a fusion protein which includes a heterologous region used to facilitate purification of the polypeptide. Many of the available peptides used for such a function allow selective binding of the fusion protein to a binding partner. A preferred binding partner includes one or more of the IgG binding domains of protein A are easily purified to homogeneity by affinity chromatography on, for example, IgG-coupled Sepharose. Alternatively, many vectors have the advantage of carrying a stretch of histidine residues that can be expressed at the N-terminal or C-terminal end of the target protein. Thus the protein of interest can be recovered by metal chelation chromatography. A nucleotide sequence encoding a recognition site for a proteolytic enzyme such as enterokinase, factor X or, procollagenase or thrombin may immediately precede the sequence for DRF1 to permit cleavage of the fusion protein to obtain the mature DRF1 protein. Additional examples of fusion partners include, but are not limited to, the yeast I-factor, the honeybee melatin leader in sf9 insect cells, 6-His tag, thioredoxin tag, hemaglutinin tag, GST tag, and OmpA signal sequence tag. As will be understood by one of skill in the art, the binding partner which recognizes and binds to the peptide may be any molecule or compound including metal ions (e.g., metal affinity columns), antibodies, or fragments thereof, and any protein or peptide which binds the peptide, such as the FLAG tag.

The polypeptides of the invention can be used as antigens for raising antibodies against the same and used to screen for compounds that modulate the activity of DRF1. DRF1 can also be used in compositions. Accordingly, the invention relates to DRF1 or an antibody according to the invention for use as a medicament as well as to the use of the molecules in the manufacture of a medicament directed towards diseases caused by uncontrolled cell growth, such as cancer. The molecules used as medicaments according to the invention may be the polypeptides or antibodies described herein as well as any novel substance identified in a screening method described herein.

In another aspect, the invention provides DRF1 polypeptides with or without associated native pattern glycosylation, acylation, sialylation, or other post-translational modifications. DRF1 expressed in yeast, insect or mammalian expression systems (discussed below) may be similar to or significantly different from a native DRF1 polypeptide in molecular weight and glycosylation pattern. Of course, expression of DRF1 in bacterial expression systems will provide non-glycosylated DRF1.

Another aspect of the present invention is directed to compositions, including pharmaceutical compositions, comprising any of the polypeptides described above and an acceptable carrier or diluent. Preferably, the carrier or diluent is pharmaceutically acceptable. Compositions comprising a polypeptide, as described above, can be used to, for example, induce antibody formation and to induce an immune response for use in, for example, vaccine preparations.

Another aspect of the present invention is directed to methods of producing a polypeptide comprising SEQ ID NO:3, or a homolog or fragment thereof, comprising introducing any of the recombinant expression vectors described above into compatible host cells, growing the host cells under conditions for expression of the polypeptide, and recovering the polypeptide from the host cells. Eukaryotic systems are preferred since they provide a variety of processing mechanisms which result in, for example, glycosylation, carboxy-terminal amidation, oxidation or derivatization of certain amino acid residues, conformational control, and so forth.

The polypeptides of the present invention are preferably provided in an isolated form, are preferably substantially purified, and most preferably are purified to homogeneity. Host cells are preferably lysed and the polypeptide is recovered from the lysate of the host cells. Alternatively, the polypeptide is recovered by purifying the cell culture medium from the host cells, preferably without lysing the host cell. The polypeptides can be recovered and purified from recombinant cell cultures by well-known methods, including ammonium sulfate or ethanol precipitation, anion or cation exchange chromatography, phosphocellulose chromatography, hydrophobic interaction chromatography, affinity chromatography, hydroxylapatite chromatography and lectin chromatography.

In addition to producing these proteins by recombinant techniques, automated amino acid synthesizers may also be employed to produce DRF1 polypeptides, or fragments a homologous protein thereof.

Another aspect of the present invention is directed to an antibody or antibodies which bind to an epitope on any of the polypeptides described herein. Preferably, the antibody binds to an epitope within SEQ ID NO:3. The antibodies according to the invention can be monoclonal or polyclonal and include individual, allelic, strain or species variants, or fragments thereof, both in their naturally occurring (full-length) forms and recombinant forms. Additionally, the antibodies are raised to the present proteins in either their native configuration or in non-native configurations. Anti-idiotypic antibodies can also be generated. Hybridomas which produce antibodies that bind to the polypeptides of the invention, and the antibodies themselves, are useful in the isolation and purification of the polypeptides. In addition, antibodies may be specific inhibitors of DRF1 activity. Antibodies which specifically bind to the polypeptides of the invention can be used to purify the protein from natural sources using well known techniques and readily available starting materials. Such antibodies can also be used to purify the protein from material present when producing the protein by recombinant DNA methodology.

Many methods of making antibodies are known to persons skilled in the art. For techniques for preparing monoclonal antibodies, see e.g. Stiites et al (eds.), *Basic and Clinical Immunology* (4$^{th}$ ed), Lange Medical Publications, Los Altos, Calif., which is incorporated herein by reference in its entirety, and references cited therein. Techniques that involve selection of libraries of recombinant antibodies in phage or similar vectors are described in Huse et al., *Science,* 1989, 246, 1275-1281, which is incorporated herein by reference in its entirety. The production of antibodies and the protein structures of complete, intact antibodies, Fab fragments and F(ab)$_2$ fragments and the organization of the genetic sequences that encode such molecules are well known and are also described, for example, in Harlow, E. and D. Lane (1988) *ANTIBODIES: A Laboratory Manual*, Cold Spring Harbor Laboratory, Cold Spring Harbor, N.Y. which is incorporated herein by reference. Briefly, for example, a polypeptide of the invention is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to the polypeptide, the hybridoma which produces them is cultured to produce a continuous supply of antibodies.

The present invention is also directed to kits, including pharmaceutical kits. The kits can comprise any of the nucleic acid molecules described above, any of the polypeptides described above, or any antibody which binds to a polypeptide of the invention as described above, as well as a negative control. The kit preferably comprises additional components, such as, for example, instructions, solid support, reagents helpful for quantification, and the like.

Another aspect of the present invention is directed to methods of inducing an immune response in a mammal against a polypeptide of the invention by administering to the mammal an amount of the polypeptide sufficient to induce an immune response. The amount will be dependent on the animal species, size of the animal, and the like but can be determined by those skilled in the art.

The following embodiments of the invention relate to several other methods of use of the polypeptides and nucleic acids of the invention. In this connection, the term "DRF1" must be interpreted to refer to either the DRF1 polypeptide (or nucleic acid encoding it, where written in lower case) per se, or to DRF1-containing complexes wherein DRF1 is physically associated with another molecule (polypeptide or nucleic acid) to produce a biologically active complex. It is also to be noted that the biological activity of the complex may be different from that of each component of the complex itself; however, the methods of use disclosed herein below are not affected by this occurrence and are referred to either DRF1 alone as well as to a DRF1-containing complex. A typical, although not limiting, example of such complex is constituted by the DRF1-CDC7 complex, which is endowed with kinase activity on physiological CDC7 kinase substrates as shown in the Examples section of the patent specification.

Therefore, it is an aspect of the present invention a method of identifying compounds which bind to either DRF1 or nucleic acid molecules encoding DRF1, comprising contacting DRF1, or a nucleic acid molecule encoding the same, with a compound, and determining whether the compound binds DRF1, or a nucleic acid molecule encoding the same. Binding can be determined by binding assays which are well known to the skilled artisan, including, but not limited to, gel-shift assays, Western blots, radiolabeled competition assay, phage-based expression cloning, co-fractionation by chromatography, co-precipitation, cross linking, interaction trap/two-hybrid analysis, southwestern analysis, ELISA, and the like, which are described in, for example, *Current Protocols in Molecular Biology,* 1999, John Wiley & Sons, NY, which is incorporated herein by reference in its entirety. The compounds to be screened include (which may include compounds which are suspected to bind DRF1, or a nucleic acid molecule encoding the same), but are not limited to, extracellular, intracellular, biologic or chemical origin. The DRF1 polypeptide or polynucleotide employed in such a test may either be free in solution, attached to a solid support, borne on a cell surface or located intracellularly. One skilled in the art can, for example, measure the formation of complexes between DRF1 and the compound being tested. Alternatively, one skilled in the art can examine the diminution in complex formation between DRF1 and its substrate caused by the compound being tested.

Another aspect of the present invention is directed to methods of identifying compounds which modulate (i.e., increase or decrease) activity of DRF1 comprising contacting DRF1 with a compound, and determining whether the compound modifies activity of DRF1. The activity in the presence of the test compound is compared to the activity in the absence of the test compound. Where the activity of the sample containing the test compound is higher than the activity in the sample lacking the test compound, the compound will have increased activity. Similarly, where the activity of the sample containing the test compound is lower than the activity in the sample lacking the test compound, the compound will have inhibited activity.

The present invention is particularly useful for screening compounds by using DRF1 in any of a variety of drug screening techniques. The compounds to be screened include (which may include compounds which are suspected to modulate DRF1 activity), but are not limited to, extracellular, intracellular, biologic or chemical origin. The DRF1 polypeptide employed in such a test may be in any form, preferably, free in solution, attached to a solid support, borne on a cell surface or located intracellularly. One skilled in the art can, for example, measure the formation of complexes between DRF1 and the compound being tested. Alternatively, one skilled in the art can examine the diminution in complex formation between DRF1 and its substrate caused by the compound being tested.

The activity of DRF1 polypeptide of the invention can be determined by, for example, kinase activity assay, cellular proliferation measurement and DNA replication activity, in the presence and absence of the test compound. These measurements can, for example, be performed as described in: Jiang and Hunter, *Proc. Natl. Acad. Sci. USA*. (1997), 94, 14320-14325; Hunter and Sefton [Editors], Methods in Enzymology (1991), 200, Academic Press, NY; Abelson, J., Simon, Melvin I., and Dunphy, W G. [Editors]., Methods in Enzymology (1997), 283, Academic Press, NY; Pagano, M. [Editor], Cell cycle: Materials and Methods, (1995), Springer-Verlag, NY.

Other assays can be used to examine enzymatic activity including, but not limited to, photometric, radiometric, HPLC, electrochemical, and the like, which are described in, for example, *Enzyme Assays: A Practical Approach*, eds. R. Eisenthal and M. J. Danson, 1992, Oxford University Press, which is incorporated herein by reference in its entirety.

In preferred embodiments of the invention, methods of screening for compounds which modulate DRF1 activity comprise contacting the compound with DRF1 and assaying for the presence of a complex between the compound and DRF1. In such assays, DRF1 is typically labeled. After suitable incubation, free DRF1 is separated from that present in bound form, and the amount of free or uncomplexed label is a measure of the ability of the particular compound to bind to DRF1.

In another embodiment of the invention, high throughput screening for compounds having suitable binding affinity to DRF1 is employed. Briefly, large numbers of different small peptide test compounds are synthesised on a solid substrate. The peptide test compounds are contacted with DRF1 and washed. Bound DRF1 is then detected by methods well known in the art.

Purified polypeptides of the invention can also be coated directly onto plates for use in the aforementioned drug screening techniques. In addition, non-neutralizing antibodies can be used to capture the protein and immobilize it on the solid support.

Other embodiments of the invention comprise using competitive screening assays in which neutralizing antibodies capable of binding a polypeptide of the invention specifically compete with a test compound for binding to the polypeptide. In this manner, the antibodies can be used to detect the presence of any peptide which shares one or more antigenic determinants with DRF1. Radiolabeled competitive binding studies are described in A. H. Lin et al. *Antimicrobial Agents and Chemotherapy*, 1997, vol. 41, no. 10. pp. 2127-2131, the disclosure of which is incorporated herein by reference in its entirety.

In other embodiments of the invention, the polypeptides of the invention are employed as a research tool for identification, characterization and purification of interacting, regulatory proteins. Appropriate labels are incorporated into the polypeptides of the invention by various methods known in the art and the polypeptides are used to capture interacting molecules. For example, molecules are incubated with the labeled polypeptides, washed to removed unbound polypeptides, and the polypeptide complex is quantified. Data obtained using different concentrations of polypeptide are used to calculate values for the number, affinity, and association of polypeptide with the protein complex.

Labeled polypeptides are also useful as reagents for the purification of molecules with which the polypeptide interacts including, but not limited to, inhibitors. In one embodiment of affinity purification, a polypeptide is covalently coupled to a chromatography column. Cells and their membranes are extracted, and various cellular subcomponents are passed over the column. Molecules bind to the column by virtue of their affinity to the polypeptide. The polypeptide-complex is recovered from the column, dissociated and the recovered molecule is subjected to protein sequencing. This amino acid sequence is then used to identity the captured molecule or to design degenerate oligonucleotides for cloning the corresponding gene from an appropriate cDNA library.

Alternatively, compounds may be identified which exhibit similar properties to DRF1 of the invention, but which are smaller and exhibits a longer half time than DRF1 in a human or animal body. When an organic compound is designed, a molecule according to the invention is used as a "lead" compound. The design of mimetics to known pharmaceutically active compounds is a well known approach in the development of pharmaceuticals based on such "lead" compounds. Mimetic design, synthesis and testing are generally used to avoid randomly screening a large number of molecules for a target property. Furthermore, structural data deriving from the analysis of the deduced amino acid sequences encoded by the DNAs of the present invention are useful to design new drugs, more specific and therefore with a higher pharmacological potency.

Comparison of the protein sequence of the present invention with the sequences present in all the available data bases showed a significant homology with the DBF4/ASK1 N-terminal motif and C-terminal motif. Accordingly, computer modelling can be used to develop a putative tertiary structure of the proteins of the invention based on the available information of other DBF4/ASK1 N-terminal motif and C-terminal motif domain proteins. Thus, novel enzyme inhibitors based on the predicted structure of DRF1 can be designed.

In a particular embodiment, the novel molecules identified by the screening methods according to the invention are low molecular weight organic molecules, in which case a composition or pharmaceutical composition can be prepared thereof for oral intake, such as in tablets. The compositions, or pharmaceutical compositions, comprising the nucleic acid molecules, vectors, polypeptides, antibodies and compounds identified by the screening methods described herein, can be prepared for any route of administration including, but not limited to, oral, intravenous, cutaneous, subcutaneous, nasal, intramuscular or intraperitoneal. The nature of the carrier or other ingredients will depend on the specific route of administration and particular embodiment of the invention to be administered. Examples of techniques and protocols that are useful in this context are, inter alia, found in Remington's Pharmaceutical Sciences, 16$^{th}$ edition, Osol, A (ed.), 1980, which is incorporated herein by reference in its entirety.

The dosage of these low molecular weight compounds will depend on the disease state or condition to be treated and other clinical factors such as weight and condition of the human or animal and the route of administration of the compound. For treating human or animals, between approximately 0.5 mg/kg of body weight to 500 mg/kg of body weight of the compound can be administered. Therapy is typically administered at lower dosages and is continued until the desired therapeutic outcome is observed.

The present compounds and methods, including nucleic acid molecules, polypeptides, antibodies, compounds identified by the screening methods described herein, have a variety of pharmaceutical applications and may be used, for example, to treat or prevent unregulated cellular growth, such as cancer cell and tumor growth. In a particular embodiment, the present molecules are used in gene therapy. For a review of gene therapy procedures, see e.g. Anderson, *Science*, 1992, 256, 808-813, which is incorporated herein by reference in its entirety.

The invention is further illustrated by way of the following examples which are intended to elucidate the invention.

These examples are not intended, nor are they to be construed, as limiting the scope of the invention. It will be clear that the invention may be practiced otherwise than as particularly described herein. Numerous modifications and variations of the present invention are possible in view of the teachings herein and, therefore, are within the scope of the invention.

Examples 1, 2, 3, 4, 5, 6 and 7 presented below are actual whereas Examples 8, 9 and 10 are prophetic. In the Examples below, "DRF1 (containing) complex(es)" indicates (a) complex(es) of DRF1 with CDC7.

Figure 3:
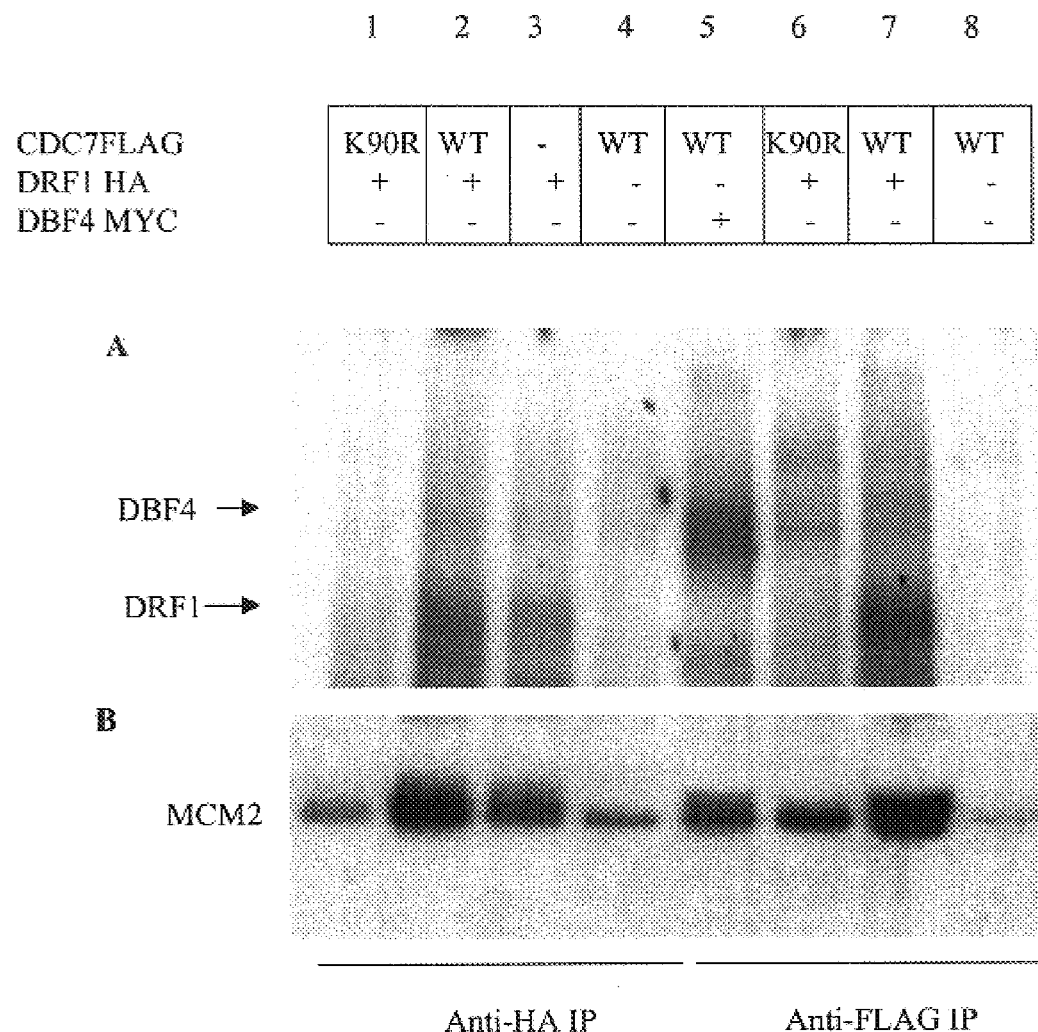

FIG. 3 demonstrates that DRF1 activates CDC7 kinase in mammalian cells: in the presence of DRF1, CDC7 is able to phosphorylate its physiological substrates MCM2. See Example 5 for more details.

Figure 4A:
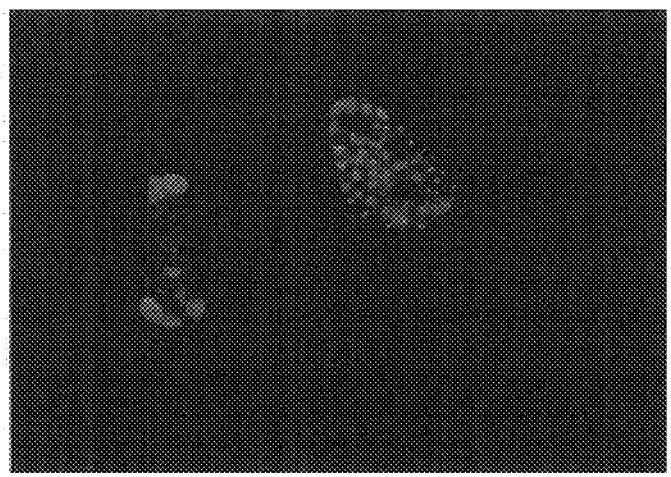
Figure 4B:
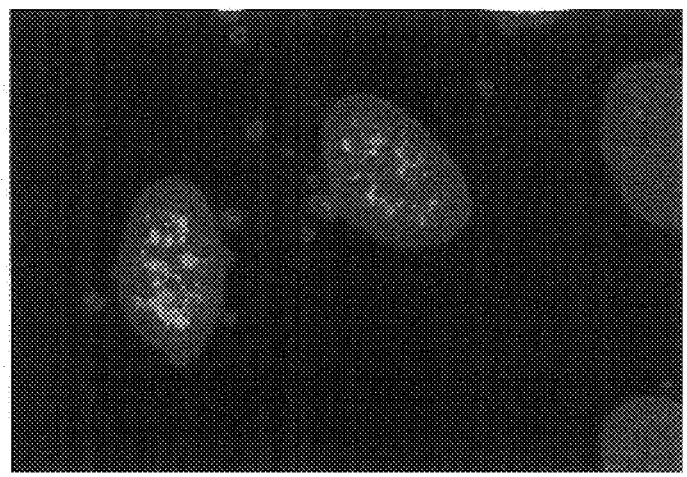
Figure 4C:
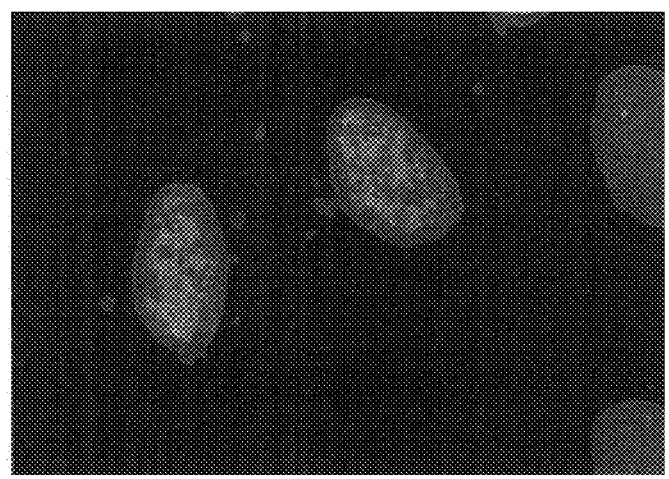
Figure 5A:
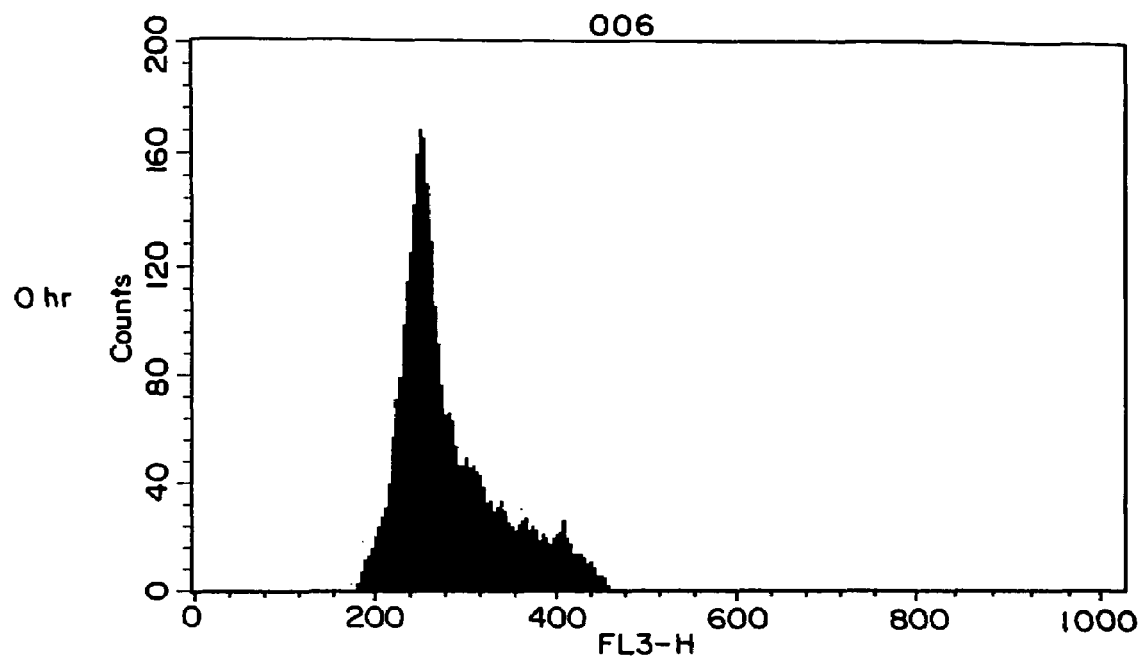
Figure 5B:
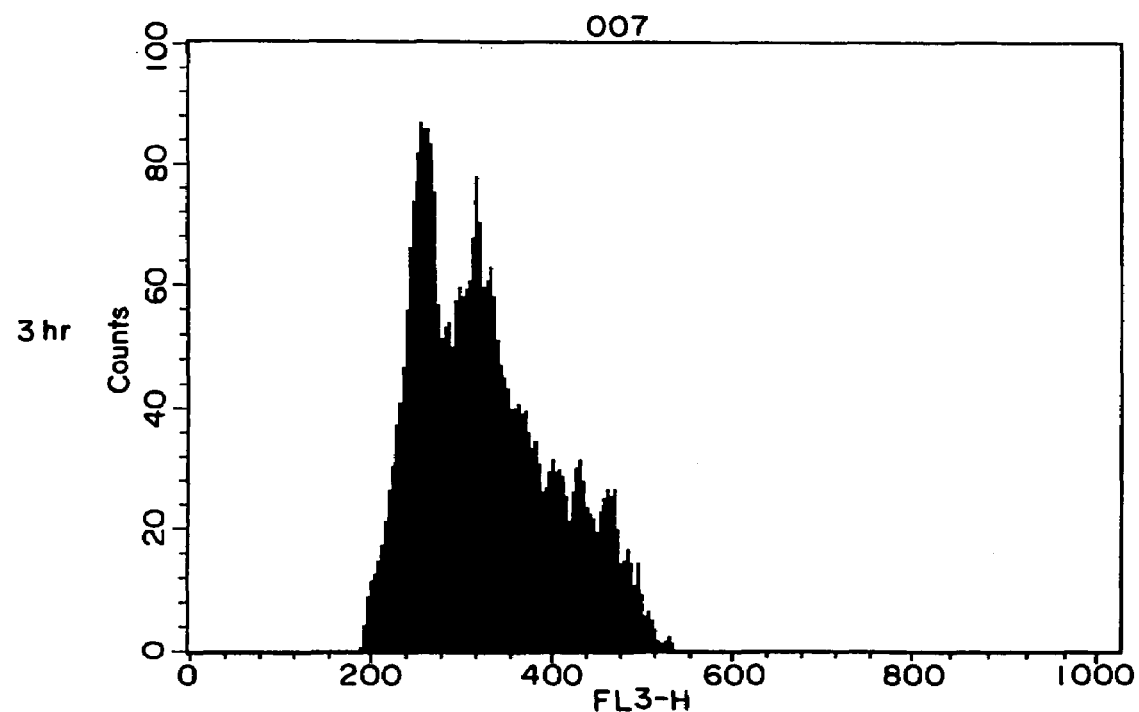
Figure 5C:
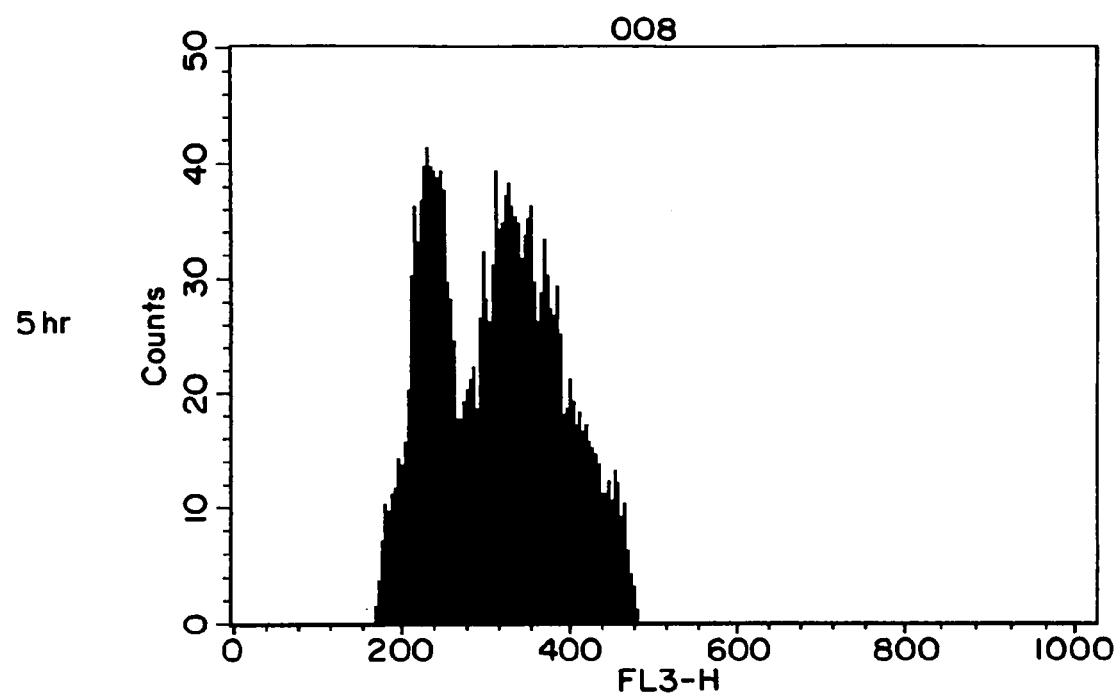
Figure 5D:
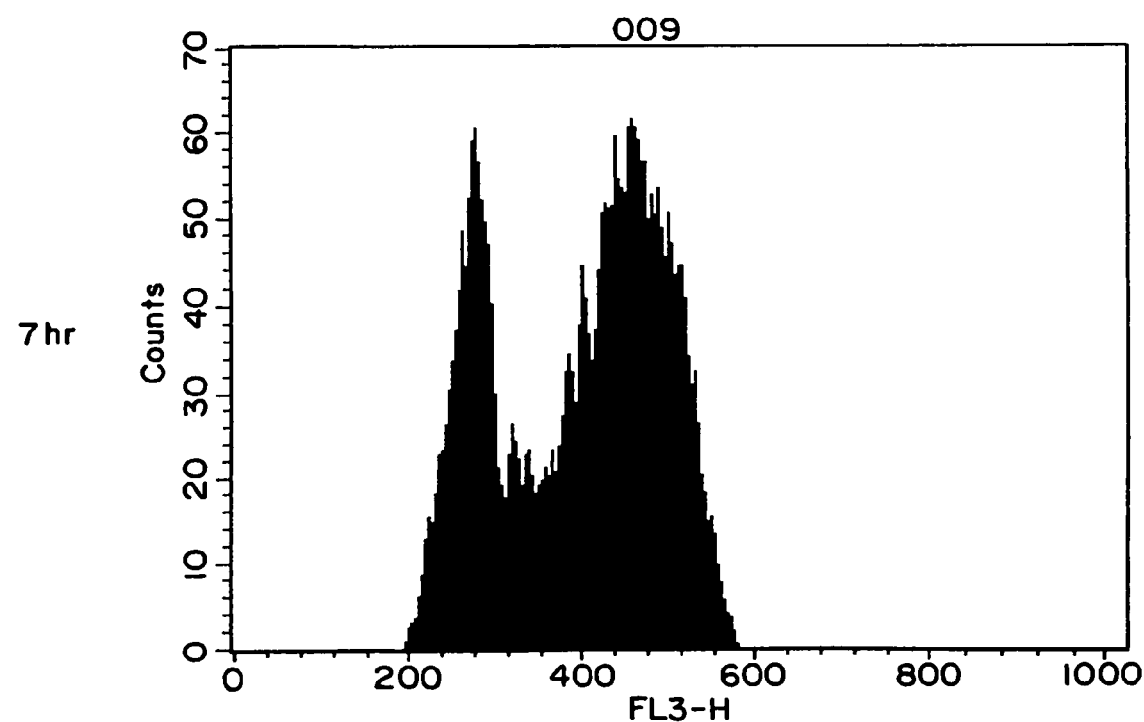
Figure 5E:
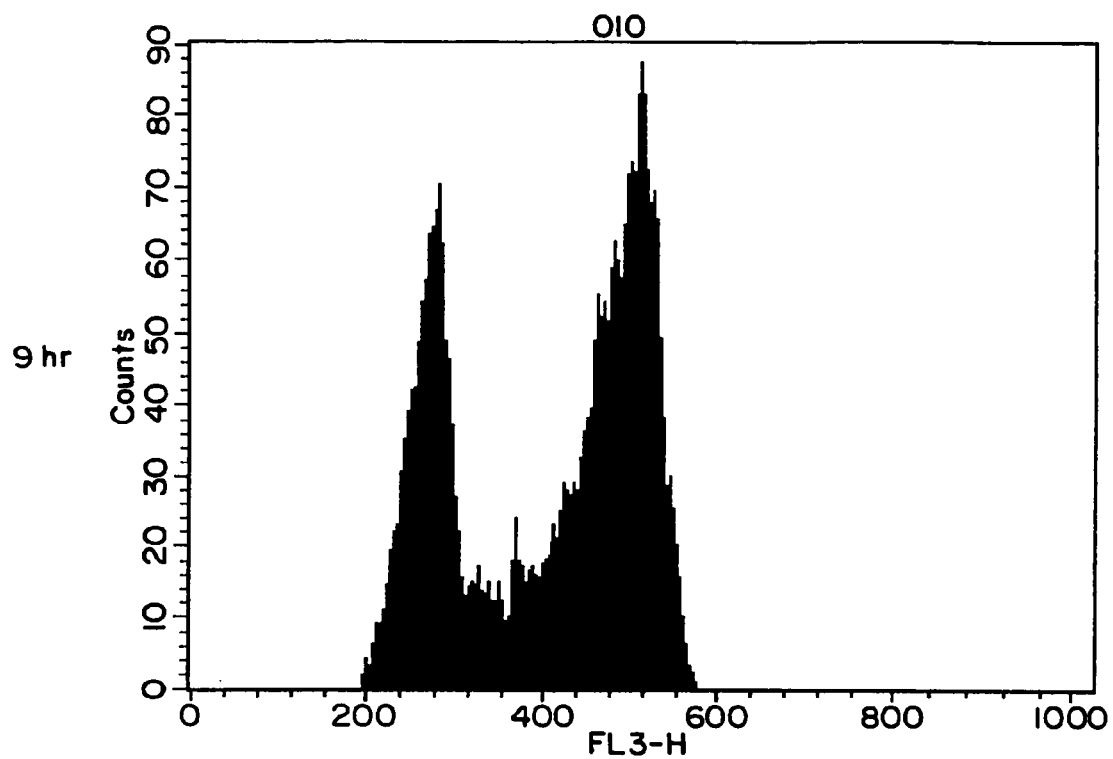
Figure 5F:
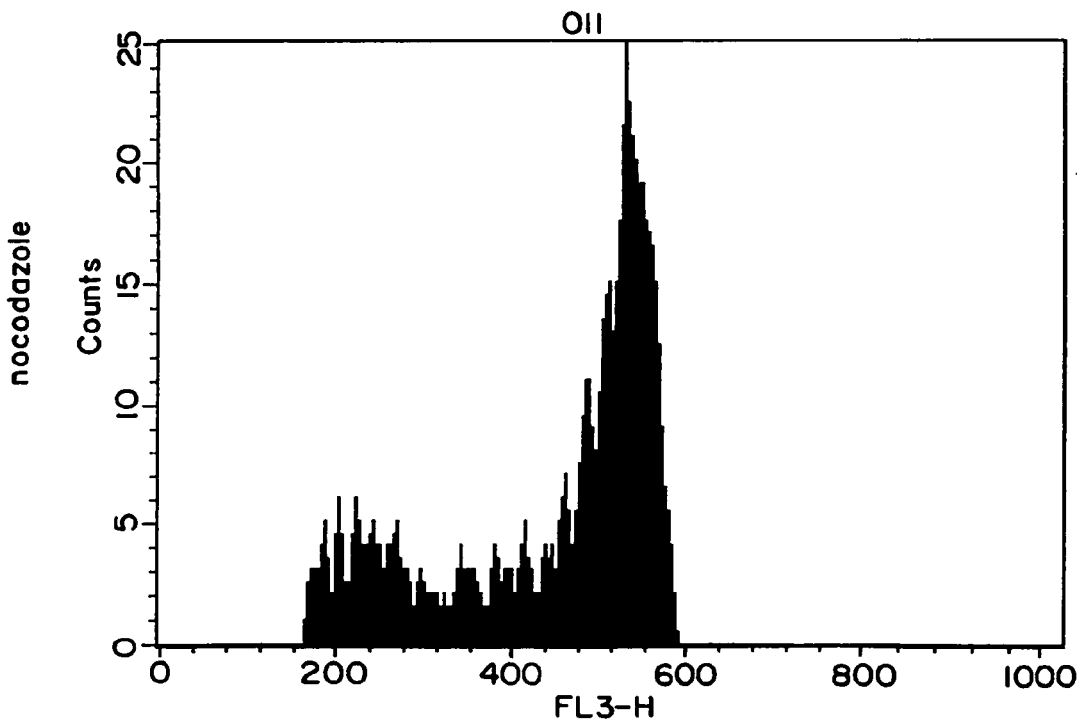

FIGS. 4A-4C shows the subcellular localization of DRF1 in mammalian cells, as evidenced by immunofluorescence microscopy. A, anti-HA immunostaining; B, DAPI staining; C, superimposing of A and B (merge). See Example 6 for more details.

FIGS. 5A-5F shows a flow cytometric analysis performed to examine the level of DRF1 expression during the cell cycle. See Example 7 for more details.

Figure 6:
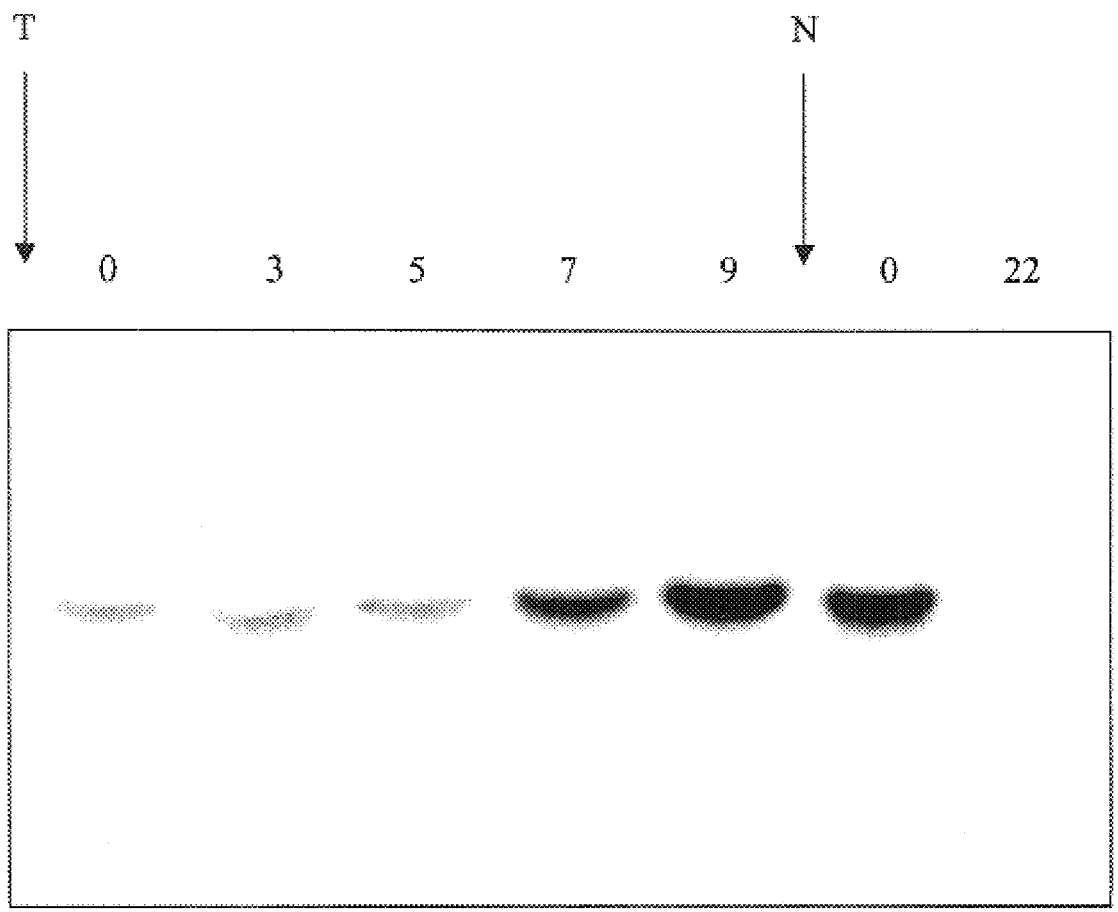

FIG. 6 is an analysis of drf1 mRNA expression by Northern Blot. T stands for Thymidine block, N stands for Nocodazole block, whereas the digits above the lanes indicate the time (in hours) after release of the block.

EXAMPLES

Example 1

Identification of Homolog of Human DBF4/ASK1

The nucleotide sequence of dbf4/ask1 cDNA (accession numbers AF160249 and NM006716), or the amino acid sequence deduced from it, was used as a query sequence against the LGtemplatesFEB2000 database Incyte proprietary database. This database, which contains previously identified and annotated sequences, was searched for regions of similarity using Gapped BLAST, (Altschul et al., *Nuc. Acids Res.*, 1997, 25, 3389, which is incorporated herein by reference in its entirety).

Briefly, the BLAST algorithm, which stands for Basic Local Alignment Search Tool is suitable for determining sequence similarity (Altschul et al., *J. Mol. Biol.*, 1990, 215, 403-410, which is incorporated herein by reference in its entirety). Software for performing BLAST analyses is publicly available through the National Center for Biotechnology Information (http://www.ncbi.nln.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extension for the word hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The Blast algorithm parameters W, T and X determine the sensitivity and speed of the alignment. The Blast program uses as defaults a word length (W) of 11, the BLOSUM62 scoring matrix (see Henikoff et al., *Proc. Natl. Acad Sci. USA*, 1992, 89, 10915-10919, which is incorporated herein by reference in its entirety) alignments (B) of 50, expectation (E) of 10, M=5, N=4, and a comparison of both strands.

The BLAST algorithm (Karlin et al., *Proc. Natl. Acad. Sci. USA*, 1993, 90, 5873-5787, which is incorporated herein by reference in its entirety) and Gapped BLAST perform a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a nucleic acid is considered similar to a drf1 gene or cDNA if the smallest sum probability in comparison of the test nucleic acid to a drf1 nucleic acid is less than about 1, preferably less than about 0.1, more preferably less than about 0.01, and most preferably less than about 0.001.

Homology searches in the LGtemplatesFEB2000 database were performed with the program BLAST version 2.0.10. The proprietary Incyte database was searched using the ASK1/DBF4 polypeptide sequence as a query sequence. Two Incyte templates with a very low score (E value lower than $10^{-8}$) were identified. The two templates (identified with numbers 150210.1 and 143458.1) were classified by Incyte as "Incyte unique", meaning no annotations were made. Incyte "template" indicates a computer-assembled sequence based upon overlapping sequence-tags, and "template" does not necessarily exist as a physical clone.

Despite the very low score, translated template 143458.1 showed, at the protein level, 40.5% of similarity and 33.3% of identity within the C terminal domain of human DBF4/ASK1. This domain is very well conserved among all DBF4/ASK1 proteins of different species, and has proved to be responsible for the binding to CDC7.

Translations of the other template, 150210.1, showed sequence similarity within the DBF4/ASK1 N-terminal portion. Also this region is as well conserved within the DBF4/ASK1 family and is known as the BRCT domain. BRCT domains are found in the breast cancer susceptibility gene 1 product (BRCA), and in several proteins involved in transcriptional regulation, DNA repair, recombination and cell cycle control. It has been proposed that CDC7-DBF4 might utilize this domain to specify its downstream targets. Despite the very low score in the BLAST search, also the 150210.1 template shows a very high sequence similarity, at the protein level, with the N-terminal portion of DBF4/ASK1 (52.6% of similarity, 37.2% of identity).

Since the N-terminal and C-terminal domains are always found together in DBF4/ASK1 proteins, we hypothesized that they could be part of the same gene and that the new gene could constitute a new human DBF4/ASK1 homologue.

A TBLASTN search against a database of genomic sequences was performed in order to verify that the two identified templates belonged to the same gene. We identified a public assembled genomic clone containing both the templates. The two Incyte templates both map on chromosome 17 clone 296K1. An exon-intron boundaries prediction of the clone was performed using GENSCAN, a gene finding algorithms that can identify complete, partial and multiple genes on both DNA strands. The program is based on a probabilistic model of gene structure/compositional properties and does not make use of protein sequence homology information (Burge, C. & Karlin, S., 1997, Prediction of complete gene structures in human genomic DNA. J. Mol. Biol. 268, 78-94).

The predicted exons were assembled by PCR analysis on cDNA libraries, thus demonstrating that the two regions were part of the same gene (see Example 2).

Two partial cDNA molecules, Incyte clone 477042 (SEQ ID NO:4) and Incyte clone 3051528 (SEQ ID N:5) from the Incyte LIFESEQ GOLD database (Feb 00 release) were completely sequenced.

Clone 3051528 represents the most 5' sequence of the 150210.1 template. The 5' end of clone 477042 partially overlaps with clone 3051528. Clone 477042 contains an open reading frame of about 600 amino acids, but lacks a starting methionine codon. Clone 3051528 contains 5' untranslated sequences, an ATG start and start of the ORF represented in clone 477042. However, clone 3051528 contains a small insertion, and two big gaps that destroy the ORF, thus this clone does not contain a valid open reading frame.

None of the two clones contain the full length cDNA sequence, nor do any of the two contain an entire open reading frame.

Example 2

Cloning of drf1 cDNA cDNAs were sequenced directly using an AB1377 fluorescence-based sequencer (Perkin Elmer/Applied Biosystems Division, PE/ABD, Foster City, Calif.) and the ABI PRISM Ready Dye-Deoxy Terminator kit with Taq FS polymerase. Each ABI cycle sequencing reaction contained about 0.5 µg of plasmid DNA. Cycle-sequencing was performed using an initial denaturation at 98° C. for 1 minute, followed by 50 cycles: 98° C. for 30 seconds, annealing at 50° C. for 30 seconds, and extension at 60° C. for 4 minutes. Temperature cycles and times were controlled by a Perkin-Ehner 9600 thermocycler. Extension products were purified using Centriflex gel filtration (Advanced Genetic Technologies Corp., Gaithersburg, Md.). Each reaction product was loaded by pipette onto the column, which was then centrifuged in a swinging bucket centrifuge (Sorvall model RT6000B table top centrifuge) at 1500×g for 4 minutes at room temperature. Column-purified samples were dried under vacuum for about 40 minutes and then dissolved in 5 µl of a DNA loading solution (83% deionized formamide, 8.3 mM EDTA, and 1.6 mg/ml Blue Dextran). The samples were then heated to 90° C. for three minutes and loaded into the gel sample wells for sequence analysis by the ABI377 sequencer. Sequence analysis was performed by importing files into the GeneWorks program (Oxford Molecular Group). Generally, sequence reads of 500 bp were obtained. Potential sequencing errors were minimized by obtaining sequence information from both DNA strands and by re-sequencing difficult areas using primers at different locations until all sequencing ambiguities were removed. The resulting sequence of the full-length cDNA is shown in SEQ ID NO:1.

To construct full-length drf1 cDNA, a PCR fragment of the most 5' sequences including 138 nucleotides of untranslated region, and a start codon at position 139, was inserted into Incyte clone 477042, which contains all of the drf1 cDNA sequences except for the most 5' sequences. In detail, a drf1 cDNA fragment was amplified by the polymerase chain reaction (PCR) method from a cDNA library. The PCR reaction mixture of 50 µl contained polymerase mixture (0.2 mM dNTPs, 1×PCR Buffer and 0.75 µl Expand High Fidelity Polymerase (Roche Biochemicals)), 1 µg of 3206491 plasmid, and 50 pmoles of forward primer 5'-AAAACGC-CAAGAGATTGATGCTGTAGC-3' (SEQ ID NO:6) and 50 pmoles of reverse primer 5'-CCCCACTGCCTCCTCCACT-GATGCTC-3' (SEQ ID NO:7) and 5 µl of a human testis tissue or HeLa cells cDNA library (Marathon PCR ready libraries, Clontech, USA). Amplification was performed in an Applied Biosystems PE9700 thermocycler, using the following program: 95° C. for 15 seconds, 59° C. for 30 seconds and 72° C. for 240 seconds; repeated for 32 cycles. The resulting 634 bp long amplified product was separated by agarose gel electrophoresis, and purified by Qiaquick gel extraction kit (Qiagen), previously inserted into a vector by TOPO-TA cloning (Invitrogen, USA). Colonies after transformation were taken, regrown, and plasmids were purified by Qiagen midiprep colums. The plasmid insert was fully sequenced on both strands. A verified PCR clone was cut with restriction enzymes EcoR1 and Xho1, and a band of 180 bp corresponding to the most 5' drf1 sequence was isolated by gel electrophoresis and purified by Qiaquick. The purified band was inserted into Incyte clone 477042, which had been linearised by restriction enzymes EcoR1 and Xho1. The resulting transformants were isolated, regrown, and plasmids were purified. Plasmids were tested by restriction analysis by EcoR1 and Xho1 for the 150 bp insert. A positive clone was then fully sequenced on both strands (SEQ ID NO: 1).

Example 3

Northern Blot Analysis

Northern blots were performed to examine the expression of drf1 mRNA. The sense orientation oligonucleotide 5'-AAAACGCCAAGAGATTGATGCTGTAGC (SEQ ID NO:6) with the antisense-orientation oligonucleotide 5'-CCCCACTGCCTCCTCCACTGATGCTC -3' (SEQ ID NO:7) were used as primers to amplify a portion of the drf1 cDNA sequence of SEQ ID NO:1. The amplified DNA fragment from positions 1 to 634 was used as a probe.

Multiple human tissue northern blots from Clontech (Human # 7760-1, Human II #7759-1, Human cancer cell lines # 7757-1) were hybridized with the probe. Pre-hybridization was carried out at 68° C. for 30' in ExpressHyb Hybridization solution (Clontech).

The probe was labeled with $\alpha$-$^{32}$P-dCTP by Multiprime DNA labelling system (Amersham Pharmacia), purified on Microspin G50 Column (Amersham Pharmacia) and added to the same hybridization solution at the final concentration of about $2\times10^6$ cpm/ml.

Hybridization was performed at 68° C. for one hour. The filters were washed several times at room temperature in 2×SSC, 0.05% SDS followed by two washes at 50° C. in 0.2×SSC, 0.1% SDS. Filters were exposed to Amersham Hyperfilm MP with intensifying screens at −80° C.

Figure 1:
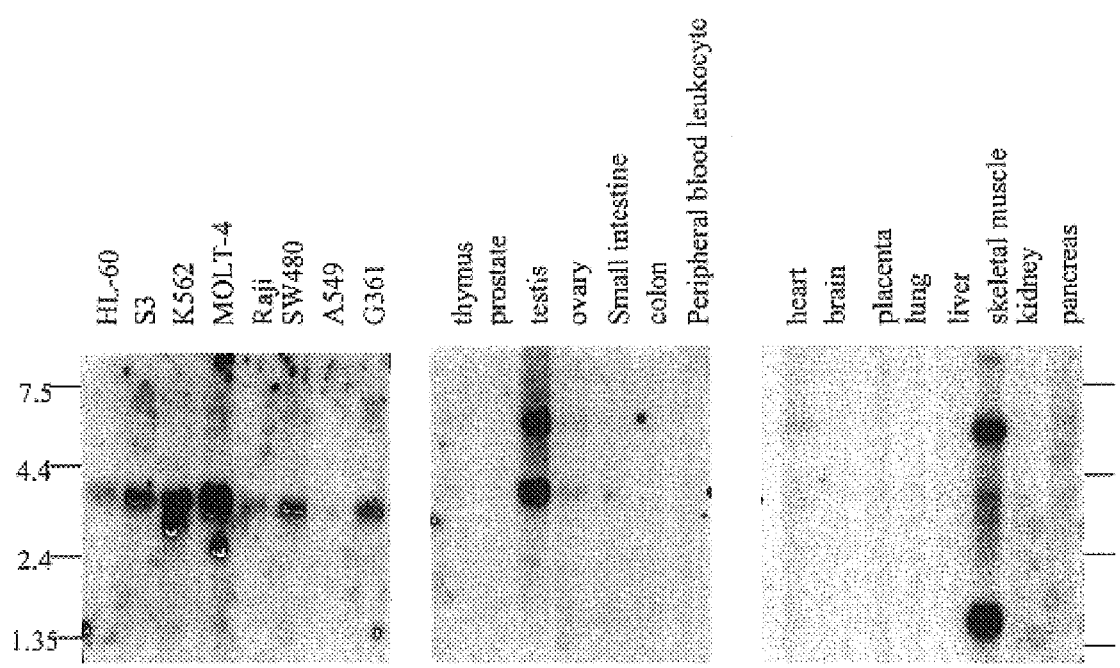
FIG. 1 shows a series of Northern Blots to analyse the expression of drf1 mRNA in different tissues. See Example 3 for more details.

Among the tissues examined, drf1 transcript of 3.1 kb was detected at high levels in testis followed by ovary (see FIG. 1). In the skeletal muscle two additional bands of 6 kb and 1.5 kb, the first one also present in other tissues, were also detected. drf1 mRNA is expressed at high levels in all the cancer cell lines examined (with the exception of A549 lung carcinoma) suggesting a role for this gene in proliferation.

Example 4

DRF1 Interacts with CDC7 Kinase in Mammalian Cells

For expression of DRF1 in mammalian cells, the drf1 coding sequence (nucleotides 138 through 1986 of SEQ ID NO:1) was cloned in the vector pCDNA1-HA (modified from the original Invitrogen pCDNA1). This vector carries an N-term HA epitope for detection of the recombinant protein with the anti-HA antibody. The forward primer for amplification of drf1 coding region is: 5'-CAGAGATCTAGCGAACCGGGAAAGGGAGAC-3' (SEQ ID NO:8) which contains a 5' extension of 9 nucleotides to introduce the BglII cloning site and 21 nucleotides matching the drf1 coding sequence without starting codon (nucleotides 4 through 25 of SEQ ID NO:2). The ATG starting codon is provided by the HA epitope at the N-terminal. The reverse primer is: 5'-TGCAGATCTCTAACCTGAGTCTACAGCCAG -3' (SEQ ID NO:9) which contains a 5' extension of 9 nucleotides to introduce a BglII restriction site for cloning and 21 nucleotides corresponding to the reverse complement of the drf1 sequence (from bases 1828 to 1849 of SEQ ID NO:2) including the stop codon. The annealing temperature used in the PCR reaction was 62° C. The PCR product was gel purified and cloned into the BglII site of the vector. Digestions with appropriate restriction enzymes were made in order to verify the right orientation of the insert in the vector. The new construct was called pCDNAHAdrf1.

To examine the ability of DRF1 to bind to CDC7 kinase in mammalian cells, pCDNAHAdrf1 plasmid, purified using Qiagen maxipreps columns, was transiently transfected in 293 cells (transformed human, primary embryonic kidney cells) together with pCdc7FLAG-tagged or the kinase negative form of CDC7 (pCdc7FLAG K90R) or control vector pCMV-Tag2 (Stratagene). For this purpose, human cdc7 cDNA was cloned in the mammalian expression vector pCMV-Tag2 that contains a CMV promoter and a FLAG epitope for antibody detection of the recombinant protein. In order to generate the kinase inactive form of CDC7 the lysine in position 90 present in the catalytic domain was mutagenized to arginine using a mutagenesis kit (Amersham).

These transfections were performed using the lipofectamine plus reagent (Gibco-BRL). 48 hours after transfection the cells were harvested, pelleted, washed with PBS and lysed in NP40 lysis buffer (1% Nonidet P-40, 50 mM Tris-Cl pH 7.5, 150 mM NaCl, 1 mM DTT) containing a cocktail of protease inhibitors (Roche cat # 1836170) and phosphatase inhibitors (NaF 50 mM, Na-ortovanadate 100 µM). Cell lysates were cleared by centrifugation, and protein concentrations were determined using the Bio-Rad protein assay kit (cat # 500-0006). 2 mg of proteins coming from different set of transfections were immunoprecipitated with anti HA antibodies (Roche cat# 1 867 423) (lanes 1 to 4) or anti-FLAG antibodies (Sigma cat # F-3165) (lanes 5 to 8) in 1 ml of NP40 lysis buffer. The immune complexes were washed three times with lysis buffer, loaded on denaturing 10% SDS-polyacrylamide gel and transferred on nitrocellulose membrane (Amersham). The presence of DRF1-HA and CDC7 in the immunoprecipitates was detected by western blot using respectively anti-HA antibodies (Roche cat# 1 867 423) or anti-CDC7 polyclonal antibodies and visualized by enhanced chemiluminescence (Amersham).

Figure 2:
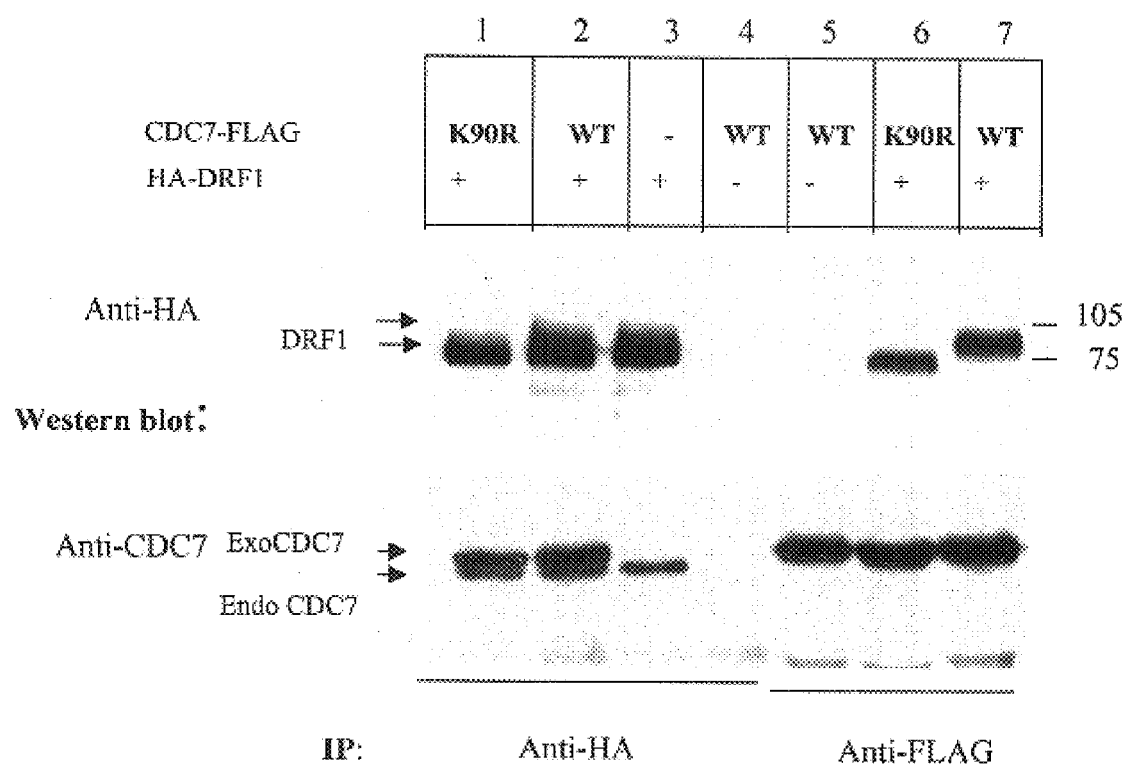
FIG. 2 illustrates a Western Blot analysis demonstrating that DRF1 interacts with CDC7. See Example 4 for more details.

As it is shown in FIG. 2, anti-HA antibodies were able to coprecipitate DRF1 together with both endogenous and over-expressed CDC7 (lanes 1-3) while the same antibody did not precipitate CDC7 when DRF1 was not expressed (lane 4). Reciprocally, anti-FLAG antibodies efficiently coprecipitated DRF1 (lanes 6 and 7). These results demonstrate that DRF1 interacts with CDC7. Both WT and mutant CDC7 were able to coprecipitate with DRF1 (compare lanes 1 and 2, and 6 and 7) with the same efficiency showing that the interaction between these two proteins is not affected by the mutation in the catalityc site. Furthermore, in presence of wild-type CDC7 or endogenous CDC7 but not of K90R CDC7, DRF1 migrated as a smear of bands, suggesting that this protein was phosphorylated by CDC7 (FIG.6, lanes 2 and 3).

Example 5

DRF1 Induces CDC7 Kinase Activity

To test if DRF1 is able to activate CDC7 kinase in mammalian cells, immunoprecipitated complexes produced as described before were tested for their ability to phosphorylate a recombinantly produced fragment of the human MCM2 protein. MCM2 amino acids 1-285 was expressed in bacteria as a GST-fusion protein and purified by glutathione-sepharose chromatography. Upon purification, the GST moiety was removed by proteolytic cleavage by the specific PreScission protease (Amersham Pharmacia Biotech) followed by absorption to glutathione-beads.

MCM2 (1-285) was chosen because it appears to be a physiological substrates of CDC7. After immunoprecipitation, the beads were further washed two times with kinase buffer (50 mM Tris-Cl pH 7.5, 10 mM $MgCl_2$, 1 mM DTT) and incubated in 25 µl of the same buffer containing 0.5 µg of MCM2, 100 µM ATP and 10 µCi [γ-32P]-ATP. The reaction was performed at 30° C. for 15 minutes and it was terminated by addition of 25 µl of 2× sample buffer and by incubation at 95° C. for 5 minutes. The reaction products were separated on denaturing 10% SDS polyacrylamide gel electrophoresis in running buffer (25 mM Tris, 192 mM glycine, 0.1% SDS). Subsequently, the gel was fixed in 10% acetic acid and 40% methanol, dried and exposed for autoradiography.

The results are shown in FIG. 3. In the presence of HA-DRF1 and wild-type CDC7, efficient phosphorylation of MCM2 (1-285) (above the background shown in lane 4, panel B) was observed in both immunoprecipitates obtained with anti-HA antibody and anti-FLAG antibody (lane 2 and 7 respectively). This kinase activity is certainly due to CDC7 because it can be abolished by overexpression of the mutant K90R (lanes 1 and 6), and it was induced by DRF1 since CDC7 alone does not have any activity (lane 8).

This result demostrated that DRF1 is a regulatory subunit of CDC7 able to induce its kinase activity in a way comparable to DBF4 (lane 5). Furthermore, DRF1, as DBF4, was detected as a phosphoprotein when expressed with wild type CDC7 but not with the kinase negative (FIG. 3, panel A). This result showed that DRF1 is activator and substrate of CDC7.

Example 6

DRF1 is Localized in the Nucleus of Mammalian Cells

The subcellular localization of DRF1 in mammalian cells was explored using indirect immunofluorescence. HeLa cells were grown to medium density on glass coverslips and transfected with pCDNA-drf1HA as described before. 24 hours after transfection the cells were rinsed with PBS three times and fixed with paraformaldeyde 4% in PBS for 20' at RT. After permeabilization in Triton 0.5%, the cells were washed and incubated with anti-HA rat antibody (ROCHE) diluted 1:25 in PBS 1% serum for 1 hour. After 3 washes with PBS, the samples were incubated for 1 hour with the secondary antibody anti-rat Texas red conjugated (Pharmingen) diluted 1:50 in PBS 1%serum. After 3 final washes in PBS coverslips were incubated with DAPI (4',6-diamidino-2-phenylindole) to stain nuclei and mounted with Mowiol.

DRF1 protein was detected by immunofluorescence microscopy in the nuclei as bright spots (FIGS. 4A-C). The localization in a subnuclear compartment was confirmed by superimposing DRF1 staining with DAPI staining (merge).

Example 7 drf1 mRNA is Cell Cycle Regulated

In order to examine the level of DRF11 expression during the cell cycle, Hela cells extracts from syncronized cultures were analyzed by northern blot.

Hela cells were blocked in G1/S phase by 2 mM thymidine treatment for 19 hours and in G2/M by treatment with nocodazole (50 ng/ml) for 16 hr. Syncronized cultures, obtained by releasing the cells from the block, were analyzed in parallel for the DNA content by flow cytometry (FIGS. 5A-5F) and for drf1 mRNA expression by northern blot (FIG. 6). For flow cytometric analysis, cells were first fixed in 70% ethanol and than stained with propidium iodide (40 ng/ml) plus RNAse A (50 ng/ml) for 30' at 37° C. Samples were than analyzed to determine the DNA content in G1, S, G2/M phases on a FACScan (Beckton-Dickinson).

The RNA for northern blot was extracted using the Rneasy mini extraction kit from Qiagen (cat. n. 74104). 30 μg of total RNA were run on gel, transferred on nitrocellulose and blotted with a drf1 cDNA probe as described before.

drf1 mRNA expression is regulated during the cell cycle, being low in G1/S, after thymidine block, and increasing with time till most of the cells appear to have a G2 DNA content. High levels of drf1 were also observed when the cells were blocked in G2/M by nocodazole treatment.

Example 8

Purification of DRF1 Protein

1. Expression of DRF1 in COS Cells

For expression of the DRF1 in COS7 cells, a polynucleotide molecule having the sequence given as nucleotides 1 through 1986 of SEQ ID NO:1 is cloned into vector pCDNA3.1 (Invitrogen, USA) plasmid, bearing the relevant DRF1 coding sequence. The plasmid contains nucleotides 1 through 1983 of SEQ ID NO:1, the V5 epitope for detection of the recombinant protein with the anti-v5 antibody, a C-terminal polyhistidine for purification with nickel chelate chromatography, and a Zeocin resistant gene for selection of stable transfectants. The forward primer for amplification of this drf1 cDNA is: 5'- AAGAATTCAAAACGCCAA-GAGATTGATGCTGTAGC-3' (SEQ ID NO:10) which contains a 5' extension of 8 nucleotides to introduce the EcoR1 cloning site and 20 nucleotides matching the drf1 sequence (nucleotides 1 through 20 of SEQ ID NO:1). The reverse primer is: 5'-AAGCGGCCGCTAACCTGAGTCTACAGC-CAG-3' (SEQ ID NO:11) which contains a 5' extension of 10 nucleotides to introduce a Not1 restriction site for cloning and 20 nucleotides corresponding to the reverse complement of the drf1 sequence from bases 1966 to 1986 of SEQ ID NO:1. The PCR conditions are 58° C. as the annealing temperature. The PCR product is gel purified and cloned into the EcoR1-NotI sites of the vector.

DRF1 expressed from a COS cell culture can be purified by preparing total cell lysates, and purifying the protein by, for example, chromatography. Purified DRF1 is concentrated to 0.5 mg/ml in an Amicon concentrator fitted with a YM-10 membrane and stored at −80° C.

2. Expression of DRF1 in Insect Cells

For expression of DRF1 in a baculovirus system, a polynucleotide molecule having the sequence given as nucleotides 139 through 158 of SEQ ID NO:1 was amplified by PCR. The forward primer is: 5'-AAGGATCCATGAGC-GAACCGGGAAAGGG-3' (SEQ ID NO:12). The first 8 nucleotides of this primer constitute a 5' extension which adds the BamHI cloning site, followed by 20 nucleotides which correspond to nucleotide residues 139 through 158 of the sequence given in SEQ ID NO:1. The reverse primer is 5'-AAGGATCCCTAACCTGAGTCTACAGCCAG-3' (SEQ ID NO:13). The first 8 nucleotides of this primer constitute a 5' extension which introduces the BamHI cloning site, followed by 20 nucleotides which correspond to the reverse complement of nucleotide residues 1966 through 1986 of the sequence given in SEQ ID NO:1.

The PCR product is gel purified, digested with BamHI, and cloned into the corresponding sites of vector pVL1393 (Pharmingen, San Diego, Calif.), which have been modified by the insertion of a GST fragment which at the 3' contains a BamHI site for insertion of drf1 coding region, producing a fusion GST-DRF1 protein. The pVL1393 expression vector contains the strong polyhedrin promoter of the *Autographa californica* nuclear polyhedrosis virus (AcM-NPV). A protein kinase site for phosphorylation and a thrombin site for excision of the recombinant protein precede the multiple cloning site is also present. Of course, many other baculovirus vectors could be used in place of pAcHTL-A, such as pAc373, pVL941 and pAcIM1. Other suitable vectors for the expression of DRF1 polypeptides can be used, provided that the vector construct includes appropriately located signals for transcription, translation, and trafficking, such as an in-frame AUG and a signal peptide, as required. Such vectors are described in Luckow et al., Virology 170:31-39, among others.

The virus is grown and isolated using standard baculovirus expression methods, such as those described in Summers et al. (*A Manual of Methods for Baculovirus Vectors and Insect Cell Culture Procedures*, Texas Agricultural Experimental Station Bulletin No. 1555 (1987)).

In a preferred embodiment, pVL1393-GST containing the drf1 gene is introduced into baculovirus using the "BaculoGold" transfection kit (Pharmingen, San Diego, Calif.) using methods established by the manufacturer. Viruses produced are re-infected twice for amplfication.

For expression of the GST-DRF1 polypeptide, High Five cells are infected with viruses. Cells are collected 48-72 hours post-infection, and lysate is prepared by sonication and centrifugation. GST-DRF1 protein can be isolated, for example by glutahione-affinity purification.

For co-expression of DRF1 with a functional partner, as for example CDC7, High Five cells are co-infected with viruses expressing the GST-DRF1 with viruses expressing, for example, CDC7 as a HIS-tagged fusion proteins. DRF1 containing complexes can then be isolated from lysates by, for example, metal-affinity purification, and verified in western blot with anti-GST antibodies.

Example 9

Interaction Trap/Two-Hybrid System

In order to assay for other DRF1-interacting proteins, the interaction trap/two-hybrid library screening method can be used. This assay was first described in Fields, et al., *Nature*, 1989, 340, 245, which is incorporated herein by reference in its entirety. A protocol is published in *Current Protocols in Molecular Biology* 1999, John Wiley & Sons, NY and Ausubel, F. M. et al. 1992, *Short protocols in molecular biology*, fourth edition, Greene and Wiley-interscience, NY, which is incorporated herein by reference in its entirety. Kits are available from Clontech, Palo Alto, Calif. (Matchmaker Two-Hybrid System 3).

A fusion of the nucleotide sequences encoding all or partial DRF1 and the yeast transcription factor GAL4 DNA-binding domain (DNA-BD) is constructed in an appropriate plasmid (ie. pGBKT7) using standard subcloning techniques. Similarly, a GAL4 active domain (AD) fusion library is constructed in a second plasmid (ie. pGADT7) from cDNA of potential DRF1-binding proteins (for protocols on forming cDNA libraries, see Sambrook et al. 1989, *Molecular cloning: a laboratory manual*, second edition, Cold Spring Harbor Press, Cold Spring Harbor, N.Y.), which is incorporated herein by reference in its entirety. The DNA-BD/DRF1 fusion construct is verified by sequencing, and tested for autonomous reporter gene activation and cell toxicity, both of which would prevent a successful two-hybrid analysis. Similar controls are performed with the AD/library fusion construct to ensure expression in host cells and lack of transcriptional activity. Yeast cells are transformed (ca. $10^5$ transformants/mg DNA) with both the DRF1 and library fusion plasmids according to standard procedure (Ausubel, et al., 1992, *Short protocols in molecular biology*, fourth edition, Greene and Wiley-interscience, NY, which is incorporated herein by reference in its entirety). In vivo binding of DNA-BD/DRF1 with AD/library proteins results in transcription of specific yeast plasmid reporter genes (ie. lacZ, HIS3, ADE2, LEU2). Yeast cells are plated on nutrient-deficient media to screen for expression of reporter genes. Colonies are dually assayed for β-galactosidase activity upon growth in Xgal (5-bromo-4-chloro-3-indolyl-β-D-galactoside) supplemented media (filter assay for -β-galactosidase activity is described in Breeden, et al., *Cold Spring Harb. Symp. Quant. Biol.,* 1985, 50, 643, which is incorporated herein by reference in its entirety). Positive AD-library plasmids are rescued from transformants and reintroduced into the original yeast strain as well as other strains containing unrelated DNA-BD fusion proteins to confirm specific DRF1/library protein interactions. Insert DNA is sequenced to verify the presence of an open reading frame fused to GAL4 AD and to determine the identity of the DRF1-binding protein.

Example 10

Assay to Identify Compounds that Modulate DRF1 Activity

For the screening purpose, a kinase substrate, for example MCM2, is biotinylated by using the EZ-link biotin Kit (Pierce, USA), as according to manufactures instruction. Purified, recombinant DRF1-containing complexes expressed in insect cells (see example 5) are accessed for kinase activity in a 80 μl reaction containing kinase buffer (50 mM HEPES pH 7.5, 10 mM $MgCl_2$, 1 mM DTT, 10 mM β-glycerophosphate (Sigma)), with 10 μM biotinylated substrate, 25 μM ATP and 0.5 μCi [γ-32P]-ATP, in the presence or absence of inhibitory compound. The reaction is performed at 30° C. for 30 minutes. The reaction is stopped by addition of excess EDTA (25mM final concentration). 50 μl of the reaction is placed in the wells of a stratavidin-coated plate (Flashplate, NEN life science), incubated for 30 minutes, and subsequently washed three times in PBS. Activity is then determined by counting the plate in a β-counter (Hewlett Packard).

Some of the preferred embodiments of the invention described above are outlined below and include, but are not limited to, the following embodiments. As those skilled in the art will appreciate, numerous changes and modifications may be made to the preferred embodiments of the invention without departing from the spirit of the invention. It is intended that all such variations fall within the scope of the invention. The entire disclosure of each publication cited herein is hereby incorporated by reference.

What is claimed is:

1. An isolated polypeptide encoded by a nucleic acid molecule, wherein said nucleic acid molecule comprises a nucleotide sequence selected from the group consisting of a) SEQ ID NO: 1, b) SEQ ID NO: 2, and c) a sequence having at least 95% identity with SEQ ID NO: 1 or SEQ ID NO: 2 and encoding an activator of CDC7 kinase activity.

2. The polypeptide of claim 1 wherein said polypeptide comprises SEQ ID NO: 3.

3. The polypeptide of claim 1 wherein said polypeptide is an activator of CDC7 kinase activity and comprises an amino acid sequence having at least 95% identity with SEQ ID NO: 3.

4. The polypeptide of claim 3 wherein said amino acid sequence having at least 95% identity with SEQ ID NO:3 comprises at least one conservative amino acid substitution compared to SEQ ID NO:3.

5. A composition comprising a polypeptide of claim 1 and an acceptable carrier or diluent.

* * * * *